(12) United States Patent
Li et al.

(10) Patent No.: US 9,550,801 B2
(45) Date of Patent: *Jan. 24, 2017

(54) SYNTHESIS OF FOUR COORDINATED PLATINUM COMPLEXES AND THEIR APPLICATIONS IN LIGHT EMITTING DEVICES THEREOF

(71) Applicant: ARIZONA BOARD OF REGENTS ACTING FOR AND ON BEHALF OF ARIZONA STATE UNIVERSITY, Scottsdale, AZ (US)

(72) Inventors: Jian Li, Tempe, AZ (US); Zixing Wang, Shanghai (CN); Eric Turner, Phoenix, AZ (US)

(73) Assignee: ARIZONA BOARD OF REGENTS ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/611,654

(22) Filed: Feb. 2, 2015

(65) Prior Publication Data

US 2015/0318500 A1 Nov. 5, 2015

Related U.S. Application Data

(63) Continuation of application No. 13/263,096, filed as application No. PCT/US2010/030095 on Apr. 6, 2010, now Pat. No. 8,946,417.

(60) Provisional application No. 61/166,901, filed on Apr. 6, 2009.

(51) Int. Cl.
| | |
|---|---|
| *C07F 15/00* | (2006.01) |
| *H01L 51/50* | (2006.01) |
| *C09K 11/06* | (2006.01) |
| *H01L 51/00* | (2006.01) |
| *H05B 33/14* | (2006.01) |
| *H01L 51/42* | (2006.01) |
| *H01L 51/56* | (2006.01) |

(52) U.S. Cl.
CPC ........... *C07F 15/0086* (2013.01); *C09K 11/06* (2013.01); *H01L 51/0087* (2013.01); *H05B 33/14* (2013.01); *C09K 2211/104* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1055* (2013.01); *C09K 2211/185* (2013.01); *H01L 51/42* (2013.01); *H01L 51/5016* (2013.01); *H01L 51/56* (2013.01); *Y02E 10/549* (2013.01); *Y02P 70/521* (2015.11)

(58) Field of Classification Search
USPC ............................................. 546/2; 313/504
See application file for complete search history.

(56) References Cited

U.S. PATENT DOCUMENTS

| | | |
|---|---|---|
| 6,780,528 B2 | 8/2004 | Tsuboyama et al. |
| 7,002,013 B1 | 2/2006 | Chi et al. |
| 7,037,599 B2 | 5/2006 | Culligan et al. |
| 7,442,797 B2 | 10/2008 | Itoh et al. |
| 7,501,190 B2 | 3/2009 | Ise |
| 7,655,322 B2 | 2/2010 | Forrest et al. |
| 7,947,383 B2 | 5/2011 | Ise et al. |
| 8,389,725 B2 | 3/2013 | Li et al. |
| 8,816,080 B2 | 8/2014 | Li et al. |
| 8,871,361 B2 | 10/2014 | Xia et al. |
| 8,927,713 B2 | 1/2015 | Li et al. |
| 8,946,417 B2 | 2/2015 | Jian et al. |
| 9,059,412 B2 | 6/2015 | Zeng et al. |
| 9,224,963 B2 | 12/2015 | Li et al. |
| 9,238,668 B2 | 1/2016 | Li et al. |
| 9,324,957 B2 | 4/2016 | Li et al. |
| 9,382,273 B2 * | 7/2016 | Li ............................. C07F 7/24 |
| 9,385,329 B2 | 7/2016 | Li et al. |
| 9,425,415 B2 | 8/2016 | Li et al. |
| 2002/0068190 A1 | 6/2002 | Tsuboyama et al. |
| 2003/0062519 A1 | 4/2003 | Yamazaki et al. |
| 2005/0260446 A1 | 11/2005 | Mackenzie et al. |
| 2006/0073359 A1 | 4/2006 | Ise et al. |
| 2006/0202197 A1 | 9/2006 | Nakayama et al. |
| 2006/0210831 A1 | 9/2006 | Sano et al. |
| 2006/0263635 A1 | 11/2006 | Ise |
| 2006/0286406 A1 | 12/2006 | Igarashi et al. |
| 2007/0057630 A1 | 3/2007 | Nishita et al. |
| 2007/0059551 A1 | 3/2007 | Yamazaki |
| 2007/0082284 A1 | 4/2007 | Stoessel et al. |
| 2007/0103060 A1 | 5/2007 | Itoh et al. |
| 2008/0001530 A1 | 1/2008 | Ise et al. |
| 2008/0036373 A1 | 2/2008 | Itoh et al. |

(Continued)

FOREIGN PATENT DOCUMENTS

| | | |
|---|---|---|
| CN | 1777663 | 5/2006 |
| CN | 1894269 | 1/2007 |

(Continued)

OTHER PUBLICATIONS

Murakami; JP 2007258550, English machine translation from EPO, Oct. 4, 2007. 80 pages.

(Continued)

*Primary Examiner* — Charanjit Aulakh
(74) *Attorney, Agent, or Firm* — Fish & Richardson P.C.

(57) ABSTRACT

Platinum complexes that exhibit photoabsorption and photoemission, methods of making such complexes, and applications thereof are disclosed, including optical devices comprising the complexes.

12 Claims, 7 Drawing Sheets

(56) References Cited

U.S. PATENT DOCUMENTS

| | | | |
|---|---|---|---|
| 2008/0054799 A1 | 3/2008 | Satou | |
| 2008/0079358 A1 | 4/2008 | Satou | |
| 2008/0241518 A1 | 10/2008 | Satou et al. | |
| 2008/0241589 A1 | 10/2008 | Fukunaga et al. | |
| 2009/0026936 A1 | 1/2009 | Satou et al. | |
| 2009/0026939 A1 | 1/2009 | Kinoshita et al. | |
| 2009/0032989 A1 | 2/2009 | Karim et al. | |
| 2009/0039768 A1 | 2/2009 | Igarashi et al. | |
| 2009/0079340 A1 | 3/2009 | Kinoshita et al. | |
| 2009/0128008 A1 | 5/2009 | Ise et al. | |
| 2009/0218561 A1 | 9/2009 | Kitamura et al. | |
| 2009/0261721 A1 | 10/2009 | Murakami et al. | |
| 2009/0267500 A1 | 10/2009 | Kinoshita et al. | |
| 2010/0000606 A1 | 1/2010 | Thompson et al. | |
| 2010/0013386 A1 | 1/2010 | Thompson et al. | |
| 2010/0171111 A1 | 7/2010 | Takada et al. | |
| 2012/0095232 A1 | 4/2012 | Li et al. | |
| 2012/0181528 A1 | 7/2012 | Takada et al. | |
| 2012/0215001 A1 | 8/2012 | Li et al. | |
| 2012/0223634 A1 | 9/2012 | Xia et al. | |
| 2012/0302753 A1 | 11/2012 | Li | |
| 2013/0048963 A1 | 2/2013 | Beers et al. | |
| 2013/0168656 A1 | 7/2013 | Tsai et al. | |
| 2013/0203996 A1 | 8/2013 | Li et al. | |
| 2013/0237706 A1 | 9/2013 | Li | |
| 2013/0341600 A1 | 12/2013 | Lin et al. | |
| 2014/0014922 A1 | 1/2014 | Lin et al. | |
| 2014/0027733 A1 | 1/2014 | Zeng et al. | |
| 2014/0084261 A1 | 3/2014 | Brooks et al. | |
| 2014/0114072 A1 | 4/2014 | Li et al. | |
| 2014/0203248 A1 | 7/2014 | Zhou et al. | |
| 2014/0330019 A1 | 11/2014 | Li et al. | |
| 2014/0364605 A1 | 12/2014 | Li et al. | |
| 2015/0008419 A1 | 1/2015 | Li | |
| 2015/0028323 A1 | 1/2015 | Xia et al. | |
| 2015/0069334 A1 | 3/2015 | Xia et al. | |
| 2015/0105556 A1 | 4/2015 | Li et al. | |
| 2015/0162552 A1 | 6/2015 | Li et al. | |
| 2015/0194616 A1 | 7/2015 | Li et al. | |
| 2015/0228914 A1 | 8/2015 | Li et al. | |
| 2015/0287938 A1 | 10/2015 | Li et al. | |
| 2015/0349279 A1 | 12/2015 | Li et al. | |
| 2016/0028028 A1 | 1/2016 | Li et al. | |
| 2016/0043331 A1 | 2/2016 | Li et al. | |
| 2016/0072082 A1 | 3/2016 | Brooks et al. | |
| 2016/0133862 A1 | 5/2016 | Li et al. | |
| 2016/0197291 A1 | 7/2016 | Li et al. | |
| 2016/0285015 A1 | 9/2016 | Li et al. | |

FOREIGN PATENT DOCUMENTS

| | | |
|---|---|---|
| CN | 101142223 A | 3/2008 |
| CN | 101667626 A | 3/2010 |
| CN | 102449108 A | 5/2012 |
| CN | 102892860 A | 1/2013 |
| CN | 102971396 A | 3/2013 |
| CN | 104232076 A | 12/2014 |
| CN | 104693243 A | 6/2015 |
| EP | 1808052 | 7/2007 |
| EP | 1874893 | 1/2008 |
| EP | 1874894 | 1/2008 |
| EP | 1919928 | 5/2008 |
| EP | 2036907 | 3/2009 |
| EP | 2096690 A2 | 9/2009 |
| EP | 2417217 | 2/2012 |
| EP | 2112213 | 7/2012 |
| EP | 2711999 | 3/2014 |
| JP | 2005267557 A | 9/2005 |
| JP | 2005310733 A | 11/2005 |
| JP | 2006047240 A | 2/2006 |
| JP | 2006232784 A | 9/2006 |
| JP | 2006242080 A | 9/2006 |
| JP | 2006242081 A | 9/2006 |
| JP | 2006256999 A | 9/2006 |
| JP | 2006257238 A | 9/2006 |
| JP | 2006261623 A | 9/2006 |
| JP | 2006290988 | 10/2006 |
| JP | 2006313796 A | 11/2006 |
| JP | 2006332622 A | 12/2006 |
| JP | 2006351638 A | 12/2006 |
| JP | 2007019462 A | 1/2007 |
| JP | 2007042875 A | 2/2007 |
| JP | 2007053132 | 3/2007 |
| JP | 2007066581 A | 3/2007 |
| JP | 2007073620 A | 3/2007 |
| JP | 2007073845 A | 3/2007 |
| JP | 2007073900 A | 3/2007 |
| JP | 2007080593 A | 3/2007 |
| JP | 2007080677 A | 3/2007 |
| JP | 2007088105 A | 4/2007 |
| JP | 2007088164 | 4/2007 |
| JP | 2007096259 A | 4/2007 |
| JP | 2007110067 A | 4/2007 |
| JP | 2007110102 A | 4/2007 |
| JP | 2007258550 A | 10/2007 |
| JP | 2007324309 A | 12/2007 |
| JP | 2008010353 A | 1/2008 |
| JP | 2008091860 A | 4/2008 |
| JP | 2008103535 A | 5/2008 |
| JP | 2008108617 A | 5/2008 |
| JP | 2008109085 A | 5/2008 |
| JP | 2008109103 A | 5/2008 |
| JP | 2008160087 A | 7/2008 |
| JP | 2008198801 A | 8/2008 |
| JP | 2008270729 A | 11/2008 |
| JP | 2008270736 A | 11/2008 |
| JP | 2009016184 A | 1/2009 |
| JP | 2009016579 A | 1/2009 |
| JP | 2009032977 A | 2/2009 |
| JP | 2009032988 A | 2/2009 |
| JP | 2009266943 A | 11/2009 |
| JP | 2009267171 | 11/2009 |
| JP | 2009267244 | 11/2009 |
| JP | 2009272339 A | 11/2009 |
| JP | 2009283891 | 12/2009 |
| JP | 2010135689 | 6/2010 |
| JP | 2012222255 A | 11/2012 |
| JP | 2013525436 | 6/2013 |
| JP | 5604505 | 10/2014 |
| JP | 2014221807 | 11/2014 |
| JP | 2015081257 | 4/2015 |
| KR | 1020060115371 | 11/2006 |
| KR | 2007061830 | 6/2007 |
| KR | 2007112465 | 11/2007 |
| KR | 1020130043460 | 4/2013 |
| TW | 200701835 | 1/2007 |
| TW | 201307365 | 2/2013 |
| WO | WO0070655 | 11/2000 |
| WO | WO2004003108 A1 | 1/2004 |
| WO | WO2004108857 | 12/2004 |
| WO | WO2005042444 | 5/2005 |
| WO | WO2005042550 | 5/2005 |
| WO | WO2006033440 | 3/2006 |
| WO | WO2006098505 | 9/2006 |
| WO | WO2006115299 | 11/2006 |
| WO | WO2006115301 | 11/2006 |
| WO | WO2007034985 A1 | 3/2007 |
| WO | WO2007069498 | 6/2007 |
| WO | WO2008066192 | 6/2008 |
| WO | WO2008066195 | 6/2008 |
| WO | WO2008066196 | 6/2008 |
| WO | WO2008117889 | 10/2008 |
| WO | WO2008123540 A2 | 10/2008 |
| WO | WO2009017211 | 2/2009 |
| WO | WO2010118026 | 10/2010 |
| WO | WO2011137429 | 11/2011 |
| WO | WO2011137431 | 11/2011 |
| WO | WO2012112853 | 8/2012 |
| WO | WO2012142387 | 10/2012 |
| WO | WO2012162488 | 11/2012 |
| WO | WO2012163471 | 12/2012 |
| WO | WO2013130483 | 9/2013 |
| WO | WO2014016611 A1 | 1/2014 |
| WO | WO2014031977 | 2/2014 |

(56) References Cited

FOREIGN PATENT DOCUMENTS

| WO | WO2014047616 | 3/2014 |
| --- | --- | --- |
| WO | WO2014109814 | 7/2014 |
| WO | WO2015027060 | 2/2015 |
| WO | WO2015131158 A1 | 9/2015 |
| WO | WO2016025921 A1 | 2/2016 |
| WO | WO2016029186 A1 | 2/2016 |

OTHER PUBLICATIONS

Murakami; JP 2007324309, English machine translation from EPO, Dec. 13, 2007, 89 pages.

Dorwald; "Side Reactions in Organic Synthesis: A Guide to Successful Synthesis Design," Chapter 1, 2005 Wiley-VCH Verlag GmbH & Co. KGaA, Wienheim, 32 pages.

Official Communication issued by the European Patent Office on Feb. 3, 2016 for Application No. 10762301.9, 5 pages.

Wong; Challenges in organometallic research—Great opportunity for solar cells and OLEDs, Journal of Organometallic Chemistry, 2009, 694, 2644-2647.

JP2009267244, English Translation from EPO, Nov. 2009, 80 pages.

JP2010135689, English translation from EPO, Jun. 2010, 95 pages.

Chi et al.; Transition-metal phosphors with cyclometalating ligands: fundamentals and applications, Chemical Society Reviews, vol. 39, No. 2, Feb. 2010, pp. 638-655.

Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.

Baldo et al., "Highly Efficient Phosphorescent Emission from Organic Electroluminescent Devices," Nature, vol. 395, Sep. 10, 1998, pp. 151-154.

Baldo et al., "Very high-efficiency green organic light-emitting devices based on electrophosphorescence," Applied Physics Letters, vol. 75, No. 1, Jul. 5, 1999, pp. 4-6.

Ji Hyun Seo et al., "Efficient blue-green organic light-emitting diodes based on heteroleptic tris-cyclometalated iridium (III) complexes". Thin Solid Films, vol. 517, pp. 1807-1810 (2009).

Official Action issued by the Japanese Patent Office on Mar. 5, 2015 for Pat. App. No. 2014-144570 filed Apr. 6, 2010, 2 pages.

Vanessa Wood et al., "Colloidal quantum dot light-emitting devices," Nano Reviews, vol. 1, 2010, 8 pages.

Glauco Ponterini et al., "Comparison of Radiationless Decay Processes in Osmium and Platinum Porphyrins," J. Am. Chem. Soc., vol. 105, No. 14, 1983, pp. 4639-4645.

Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.

Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.

Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.

Evan L. Williams et al., "Excimer-Based White Phosphorescent Organic Light Emitting Diodes with Nearly 100% Internal Quantum Efficiency," Adv. Mater., vol. 19, 2007, pp. 197-202.

Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.

Ke Feng et al., "Norbornene-Based Copolymers Containing Platinum Complexes and Bis(carbazolyl)benzene Groups in Their Side-Chains," Macromolecules, vol. 42, 2009, pp. 6855-6864.

Chi-Ming Che et al., "Photophysical Properties and OLED Applications of Phosphorescent Platinum(II) Schiff Base Complexes," Chem. Eur. J., vol. 16, 2010, pp. 233-247.

Stephen R. Forrest, "The path to ubiquitous and low-cost organic electronic appliances on plastic," Nature, vol. 428, Apr. 29, 2004, pp. 911-918.

Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.

Xiaofan Ren et al., "Ultrahigh Energy Gap Hosts in Deep Blue Organic Electrophosphorescent Devices," Chem. Mater., vol. 16, 2004, pp. 4743-4747.

First Office Action issued on Jun. 26, 2013 by the Chinese patent Office for Application No. 201080024040.X filed Apr. 6, 2010 (Applicant—Arizona Board of Regents / Inventors—Jian Li, et al.) (pp. 1-16).

Official Communication issued by the European Patent Office on Oct. 2, 2012 for Application No. 10762301.9 filed Apr. 6, 2010 (Applicant—Arizona Board of Regents / Inventors—Jian Li, et al.) (p. 1).

Extended Search Report issued by the European Patent Office on Sep. 13, 2012 for Application No. 10762301.9 filed Apr. 6, 2010 (Applicant—Arizona Board of Regents / Inventors—Jian Li, et al.) (pp. 1-7).

Amendments Received Before Examination filed with the European Patent Office on Mar. 9, 2012 for Application No. 10762301 filed Apr. 6, 2010 (Applicant—Arizona Board of Regents / Inventors—Jian Li, et al.)(pp. 1-8).

Official Communication issued by the European Patent Office on Dec. 7, 2011 for Application No. 10762301.9 filed Apr. 6, 2010 (Applicant—Arizona Board of Regents / Inventors—Jian Li, et al.) (pp. 1-2).

International Preliminary Report on Patentability issued by the International Searching Authority on Oct. 11, 2011 for PCT/US2010/030095 filed Apr. 6, 2010 and published as WO 2010/118026 on Oct. 14, 2010 (Applicant—Arizona Board of Regents / Inventors—Jian Li, et al.) (pp. 1-5).

International Search Report mailed by the International Searching Authority on Nov. 16, 2010 for PCT/US2010/030095 filed Apr. 6, 2010 and published as WO 2010/118026 on Oct. 14, 2010 (Applicant—Arizona Board of Regents / Inventors—Jian Li, et al.) (pp. 1-4).

Written Opinion issued by the International Searching Authority on Nov. 16, 2010 for PCT/US2010/030095 filed Apr. 6, 2010 and published as WO 2010/118026 on Oct. 14, 2010 (Applicant—Arizona Board of Regents / Inventors—Jian Li, et al.) (pp. 1-4).

Second Office Action issued by the Chinese Patent Office on Mar. 7, 2014 for Pat. App. No. 201080024040.X filed Apr. 6, 2010 and published as CN 102449108A on May 9, 2012 (Applicants—Arizona Technology Enterprises (AZTE); Inventors—Li et al.) (6 pages).

English Translation of Second Office Action issued by the Chinese Patent Office on Mar. 7, 2014 for Pat. App. No. 201080024040.X filed Apr. 6, 2010 and published as CN 1024491 08A on May 9, 2012 (Applicants—Arizona Technology Enterprises (AZTE); Inventors—Li et al.) (7 pages).

Response to Office Action (and English Translation) filed with the Chinese Patent Office on Jan. 13, 2014 for Pat. App. No. 201080024040.X filed Apr. 6, 2010 and published as Cn1 024491 08A on May 9, 2012 (Applicants—Arizona Technology Enterprises (AZTE); Inventors—Li et al.) (16 pages).

Official Action issued by the Japanese Patent Office on Mar. 13, 2014 for Pat. App. No. 2012-504779 filed Apr. 6, 2010 and published as JP 2012-522843 on Sep. 27, 2012 (Applicants—Arizona Technology Enterprises (AZTE); Inventors—Li et al.) (5 pages).

Official Action (English translation only) issued by the Japanese Patent Office on Mar. 13, 2014 for Pat. App. No. 2012-504779 filed Apr. 6, 2010 and published as JP 2012-522843 on Sep. 27, 2012 (Applicants—Arizona Technology Enterprises (AZTE); Inventors—Li et al) (8 pages).

English Translation of Third Office Action issued by the Chinese Patent Office on Oct. 27, 2014 for Pat. App. No. 201080024040.X filed Apr. 6, 2010 and published as CN 1024491 08A on May 9, 2012 (Applicants—Arizona Technology Enterprises (AZTE); Inventors—Li et al.) (13 pages).

(56) References Cited

OTHER PUBLICATIONS

Official Communication issued by the European Patent Office on Aug. 1, 2016 for Application No. 10762301.9, 4 pages.
Marc Lepeltier et al., "Efficient blue green organic light-emitting devices based on a monofluorinated heteroleptic iridium(III) complex," Synthetic Metals, vol. 199, 2015, pp. 139-146.
Stefan Bernhard, "The First Six Years: A Report," Department of Chemistry, Princeton University, May 2008, 11 pages.

* cited by examiner

SYNTHESIS OF FOUR COORDINATED PLATINUM COMPLEXES AND THEIR APPLICATIONS IN LIGHT EMITTING DEVICES THEREOF

CROSS REFERENCE TO RELATED APPLICATIONS

The present application is a continuation of U.S. patent application Ser. No. 13/263,096, filed Jan. 3, 2012, which is a National Phase Application of International Application No. PCT/US2010/030095, filed Apr. 6, 2010, which claims priority to U.S. Provisional Patent Application No. 61/166,901, filed on Apr. 6, 2009, all of which are hereby incorporated by reference in their entirety.

BACKGROUND

Technical Field

The present disclosure relates to platinum complexes, and specifically to platinum complexes which are capable of absorbing and/or emitting light and are thus useful as emissive or absorption materials.

Technical Background

Compounds capable of absorbing and/or emitting light are ideally suited for use in a wide variety of optical and electro-optical devices, including photo-absorbing devices such as solar- and photo-sensitive devices, photo-emitting devices, such as organic light emitting diodes (OLEDs), or devices capable of both photo-absorption and emission. Much research has been devoted to the discovery and optimization of organic and organometallic materials for use in optical and electro-optical devices. Generally, research in this area aims to accomplish a number of goals, including improvements in absorption and emission efficiency, as well as improvements in processing ability, among others.

Despite significant advances in research devoted to optical and electro-optical materials, many current devices comprising organic or organometallic materials have yet to be optimized. Many materials currently used in optical and electro-optical devices have a number disadvantages, including poor processing ability, inefficient emission or absorption, and less than ideal stability, among others. Thus, a need exists for new materials which exhibit improved performance in optical and electro-optical devices. This need and other needs are satisfied by the present invention.

SUMMARY

The present invention relates to platinum complexes that exhibit photoabsorpstion and photoemission, to methods of making such compounds, and to applications thereof, including optical devices comprising the compounds.

In one aspect, the compounds are represented by the formula:

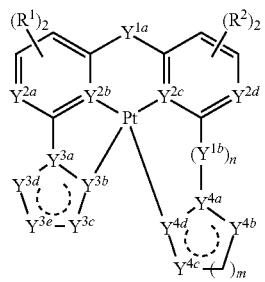

wherein each $R^1$ and $R^2$ in $(R^1)_2$ and $(R^2)_2$ independently represents hydrogen, optionally substituted $C_1$-$C_4$ alkyl, halogen, hydroxyl, amino, nitro, or thiol;

$R^3$ represents methyl, ethyl, propyl, or butyl;

$Y^{1a}$ represents O, S, $NR^{4a}$, wherein $R^{4a}$ represents optionally substituted $C_1$-$C_4$ alkyl; $Si(R^{4b})_2$, wherein each $R^{4b}$ in $(R^{4b})_2$ independently represents optionally substituted $C_1$-$C_4$ alkyl; or $C(R^{4c})_2$, wherein each $R^{4c}$ in $(R^{4c})_2$ represents hydrogen or optionally substituted $C_1$-$C_4$ alkyl;

n is an integer 0 or 1;

$Y^{1b}$, when present, represents O, S, $NR^{5a}$, wherein $R^{5a}$ represents optionally substituted $C_1$-$C_4$ alkyl; $Si(R^{5b})_2$, wherein each $R^{5b}$ in $(R^{5b})_2$ independently represents optionally substituted $C_1$-$C_4$ alkyl; or $C(R^{5c})_2$, wherein each $R^{5c}$ in $(R^{5c})_2$ represents hydrogen or optionally substituted $C_1$-$C_4$ alkyl;

each of $Y^{2a}$, $Y^{2b}$, $Y^{2c}$, and $Y^{2d}$ independently represents N, $NR^{6a}$, or $CR^{6b}$, wherein each of $R^{6a}$ and $R^{6b}$ independently represents hydrogen, optionally substituted $C_1$-$C_4$ alkyl, halogen, hydroxyl, amino, nitro, or thiol;

each of $Y^{3a}$, $Y^{3b}$, $Y^{3c}$, $Y^{3d}$, $Y^{3e}$, $Y^{4a}$, $Y^{4b}$, $Y^{4c}$, and $Y^{4d}$ independently represents N, O, S, $NR^{6a}$, $CR^{6b}$, wherein each of $R^{6a}$ and $R^{6b}$ independently represents hydrogen or optionally substituted $C_1$-$C_4$ alkyl; or $Z(R^{6c})_2$, wherein Z is C or Si, and wherein each $R^{6c}$ in $(R^{6c})_2$ independently represents hydrogen or optionally substituted $C_1$-$C_4$ alkyl;

wherein m is an integer 1 or 2;

wherein the open dotted circle

indicates partial or full unsaturation of the ring with which it is associated;

provided that if m is 1, each of $Y^{2a}$ and $Y^{2d}$ is CH and each of $Y^{2b}$ and $Y^{2c}$ is N, then at least one of $Y^{4a}$, $Y^{4b}$, $Y^{3a}$, or $Y^{3d}$ is not N; and provided that if n is 0, m is 2, each of $Y^{2a}$ and $Y^{2d}$ is CH, and each of $Y^{2b}$ and $Y^{2c}$ is N, then at least one of $Y^{3b}$ or $Y^{3c}$ is not N.

Also disclosed are optical devices, such as organic light emitting devices, photovoltaic devices (e.g., solar cells), and luminescent display devices that comprise one or more compounds of the invention as a functional material, such as a light-emitter or absorber, or both.

BRIEF DESCRIPTION OF THE FIGURES

The accompanying figures, which are incorporated in and constitute a part of this specification, illustrate several aspects and together with the description serve to explain the principles of the invention.

Figure 1:
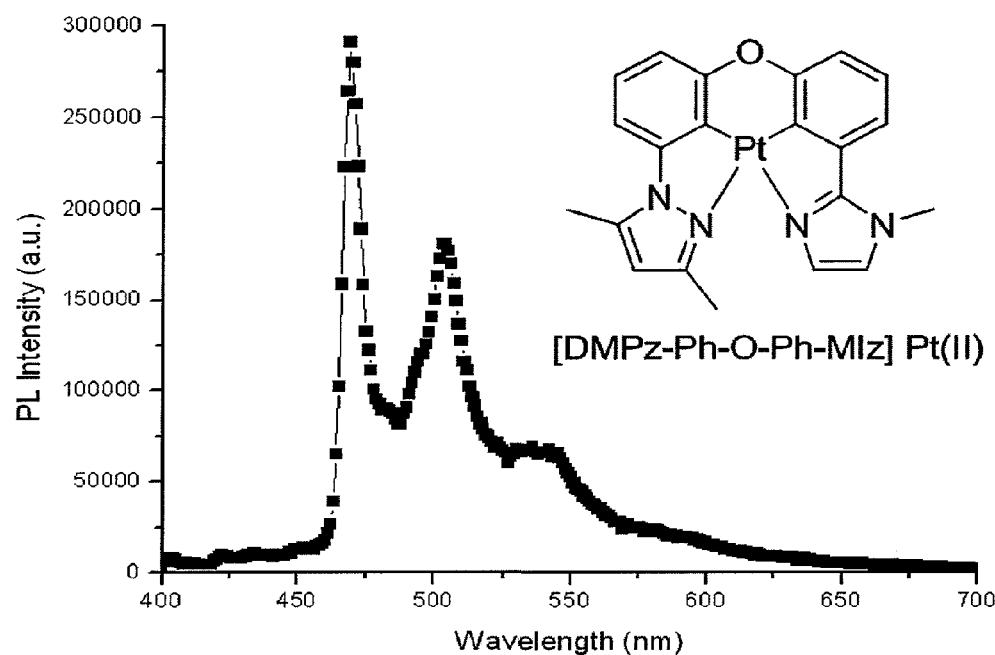
FIG. 1 is a photoluminescence spectrum produced from a specific aspect, [DMPz-Ph-O-Ph-MIz] Pt (II) taken in dichloromethane at 77 K.

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

As used in the specification and the appended claims, the singular forms "a," "an" and "the" include plural referents unless the context clearly dictates otherwise. Thus, for example, reference to "a component" includes mixtures of two or more components.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

The terms "amine" or "amino" as used herein are represented by the formula NA$^1$A$^2$A$^3$, where A$^1$, A$^2$, and A$^3$ can be, independently, hydrogen or optionally substituted alkyl, cycloalkyl, alkenyl, cycloalkenyl, alkynyl, cycloalkynyl, aryl, or heteroaryl group as described herein.

The term "halide" as used herein refers to the halogens fluorine, chlorine, bromine, and iodine.

The term "hydroxyl" as used herein is represented by the formula —OH.

The term "nitro" as used herein is represented by the formula —NO$_2$.

The term "nitrile" as used herein is represented by the formula —CN.

The term "thiol" as used herein is represented by the formula —SH.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

In one aspect, the compounds of the present invention can be represented by the formula:

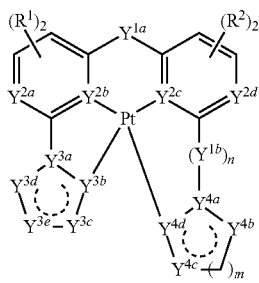

In such an aspect, each $R^1$ and $R^2$ in $(R^1)_2$ and $(R^2)_2$ independently represents hydrogen, optionally substituted $C_1$-$C_4$ alkyl, halogen, hydroxyl, amino, nitro, or thiol; $R^3$ represents methyl, ethyl, propyl, or butyl; $Y^{1a}$ represents O, S, $NR^{4a}$, wherein $R^{4a}$ represents optionally substituted $C_1$-$C_4$ alkyl; $Si(R^{4b})_2$, wherein each $R^{4b}$ in $(R^{4b})_2$ independently represents optionally substituted $C_1$-$C_4$ alkyl; or $C(R^{4c})_2$, wherein each $R^{4c}$ in $(R^{4c})_2$ represents hydrogen or optionally substituted $C_1$-$C_4$ alkyl; n is an integer 0 or 1; $Y^{1b}$, when present, represents O, S, $NR^{5a}$, wherein $R^{5a}$ represents optionally substituted $C_1$-$C_4$ alkyl; $Si(R^{5b})_2$, wherein each $R^{5b}$ in $(R^{5b})_2$ independently represents optionally substituted $C_1$-$C_4$ alkyl; or $C(R^{5c})_2$, wherein each $R^{5c}$ in $(R^{5c})_2$ represents hydrogen or optionally substituted $C_1$-$C_4$ alkyl; each of $Y^{2a}$, $Y^{2b}$, $Y^{2c}$, and $Y^{2d}$ independently represents N, $NR^{6a}$, or $CR^{6b}$, wherein each of $R^{6a}$ and $R^{6b}$ independently represents hydrogen, optionally substituted $C_1$-$C_4$ alkyl, halogen, hydroxyl, amino, nitro, or thiol; each of $Y^{3a}$, $Y^{3b}$, $Y^{3c}$, $Y^{3d}$, $Y^{3e}$, $Y^{4a}$, $Y^{4b}$, $Y^{4c}$, and $Y_{4d}$ independently represents N, O, S, $NR^{6a}$, $CR^{6b}$, wherein each of $R^{6a}$ and $R^{6b}$ independently represents hydrogen or optionally substituted $C_1$-$C_4$ alkyl; or $Z(R^{6c})_2$, wherein Z is C or Si, and wherein each $R^{6c}$ in $(R^{6c})_2$ independently represents hydrogen or optionally substituted $C_1$-$C_4$ alkyl; m is an integer 1 or 2; wherein the open dotted circle ( )

indicates partial or full unsaturation of the ring with which it is associated.

In one aspect of the formula above, if m is 1, each of $Y^{2a}$ and $Y^{2d}$ is CH and each of $Y^{2b}$ and $Y^{2c}$ is N, then at least one of $Y^{4a}$, $Y^{4b}$, $Y^{3a}$, or $Y^{3d}$ is not N. For example, according to this aspect, the following compound is not included in the above formula:

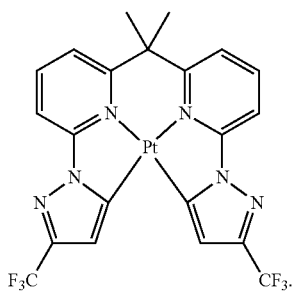

As can be seen in the preceding example above, m is 1, each of $Y^{2a}$ and $Y^{2d}$ is CH and each of $Y^{2b}$ and $Y^{2c}$ is N. However, each of $Y^{4a}$, $Y^{4b}$, $Y^{3a}$, or $Y^{3d}$ is N. It follows that the preceding example, according to this aspect, is not included within the general formula above. In the practice of this aspect, similar analysis can be used to determine whether or not a compound is or is not included within the general formula above.

In a further aspect of the general formula above, if n is 0, m is 2, each of $Y^{2a}$ and $Y^{2d}$ is CH, and each of $Y^{2b}$ and $Y^{2c}$ is N, then at least one of $Y^{3b}$ or $Y^{3c}$ is not N. For example, according to this aspect, the following compound is not included in the above formula:

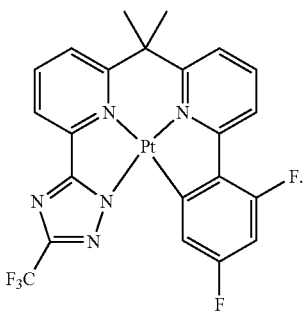

As can be seen in the preceding example above, n is 0, m is 2, each of $Y^{2a}$ and $Y^{2d}$ is CH, and each of $Y^{2b}$ and $Y^{2c}$ is N. However, each of $Y^{3b}$ and $Y^{3c}$ is N. It follows that the preceding example, according to this aspect, is not included within the general formula above. Once more, in the practice of this aspect, similar analysis can be used to determine whether or not a compound is or is not included within the general formula above.

In one aspect of the general formula above, the compound is represented by the formula:

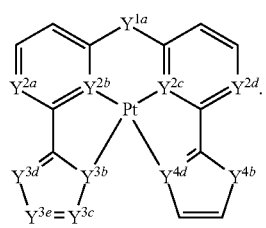

In other non-limiting aspects, examples of specific aspects within this formula can include one or more of the following:

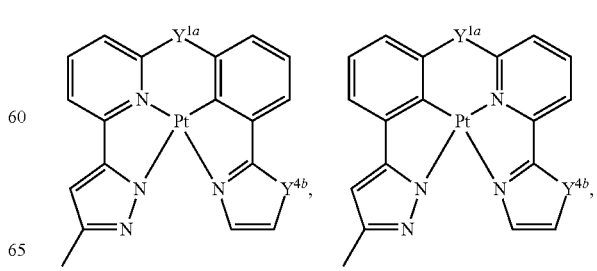

-continued

In other non-limiting aspects, examples of specific aspects within this formula can include one or more of the following:

In another aspect of the general formula above, the compound is represented by the formula:

In other aspects, non-limiting examples of specific aspects within this formula can include one or more of the following:

-continued

In other aspects, non-limiting examples of specific aspects within this formula can include one or more of the following:

In other aspects, non-limiting examples of specific aspects within this formula can include one or more of the following:

In other aspects, non-limiting examples of specific aspects within this formula can include one or more of the following:

-continued

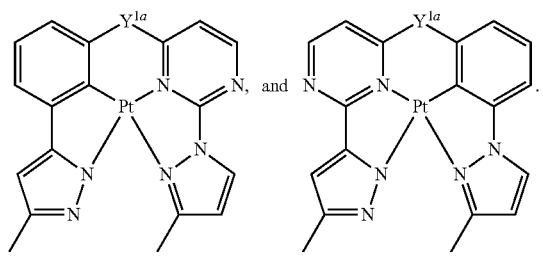

In other aspects, non-limiting examples of specific aspects within this formula can include one or more of the following:

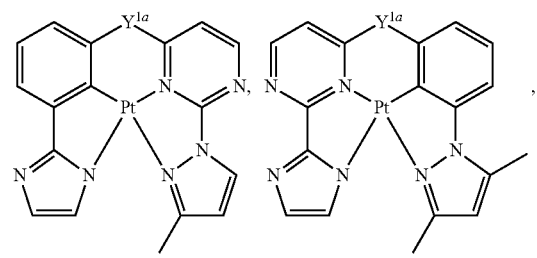

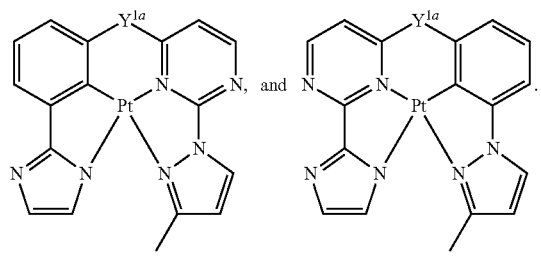

In other aspects, non-limiting examples of specific aspects within this formula can include one or more of the following:

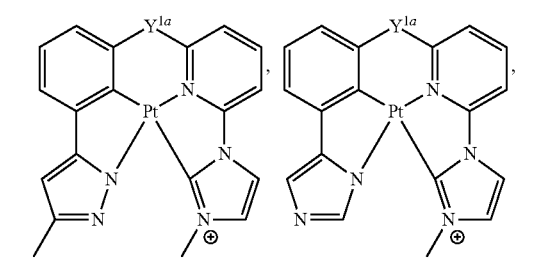

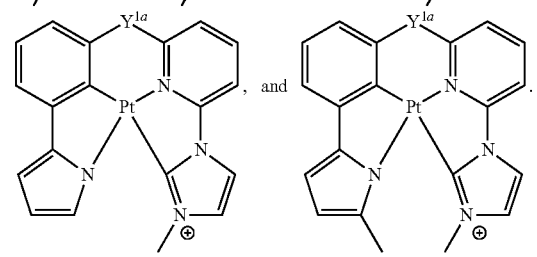

In other aspects, non-limiting examples of specific aspects within this formula can include one or more of the following:

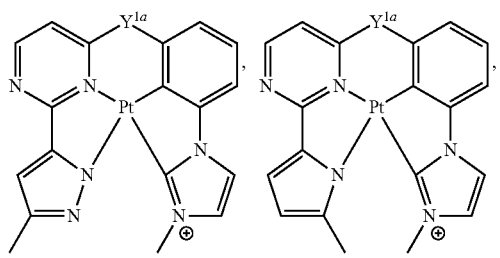

In other aspects, non-limiting examples of specific aspects within this formula can include one or more of the following:

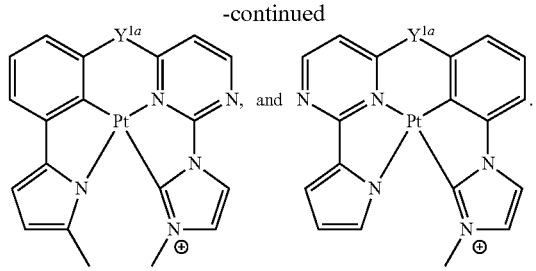

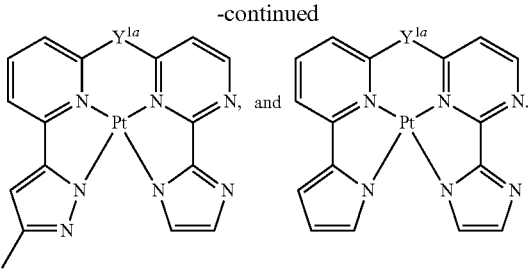

In another aspect of the general formula above, the compound is represented by the formula:

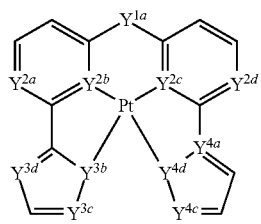

In other aspects, non-limiting examples of specific aspects within this formula can include one or more of the following:

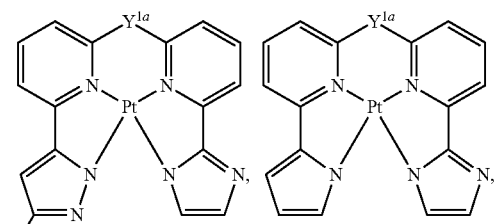

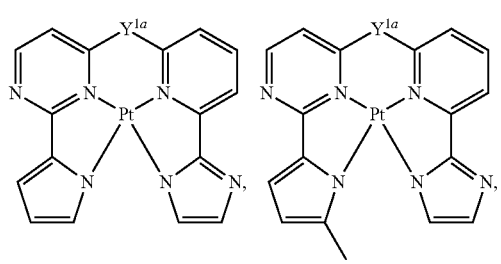

In other aspects, non-limiting examples of specific aspects within this formula can include one or more of the following:

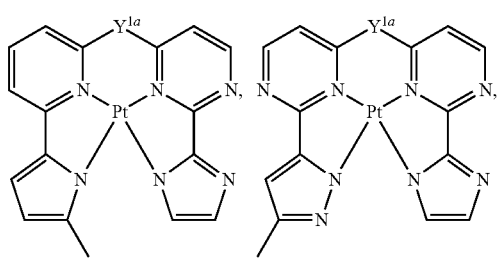

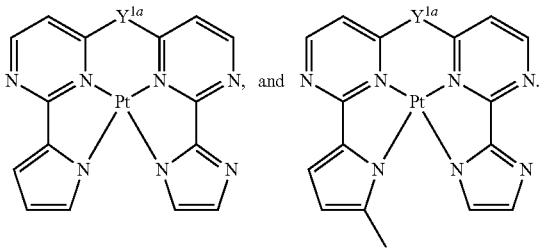

In another aspect of the general formula above, the compound is represented by the formula:

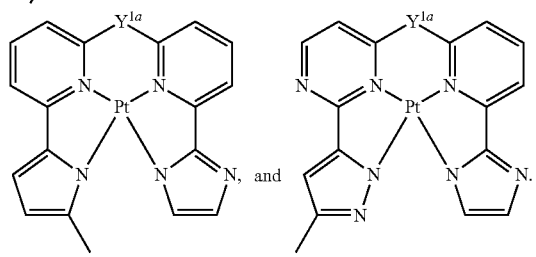

In other aspects, non-limiting examples of specific aspects within this formula can include one or more of the following:

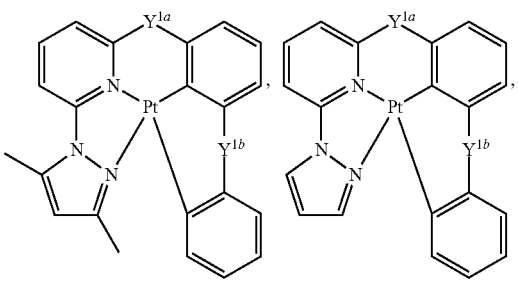

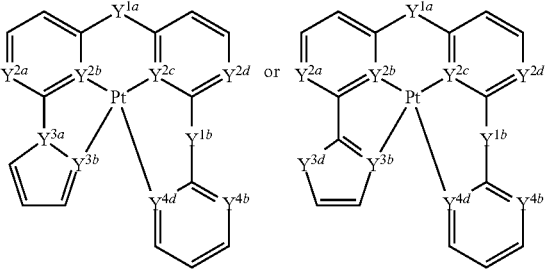

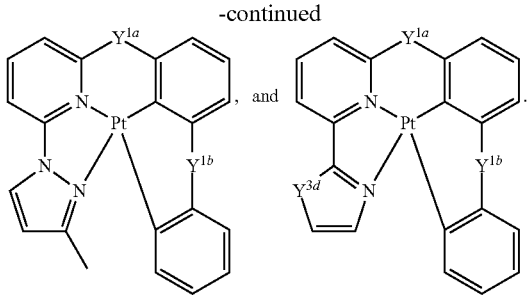

In other aspects, non-limiting examples of specific aspects within this formula

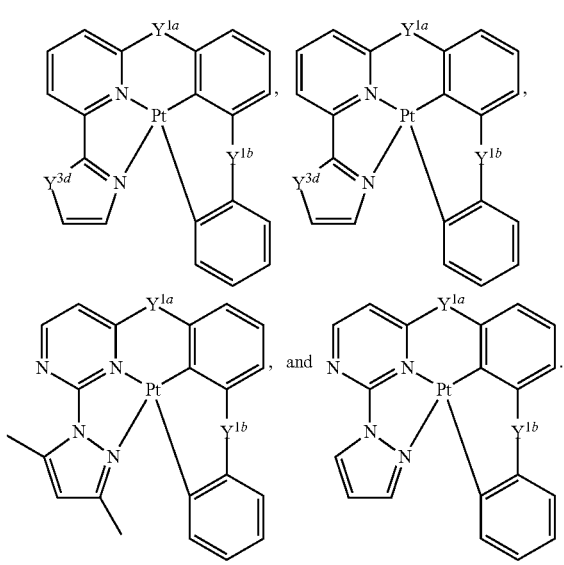

In other aspects, non-limiting examples of specific aspects within this formula can include one or more of the following:

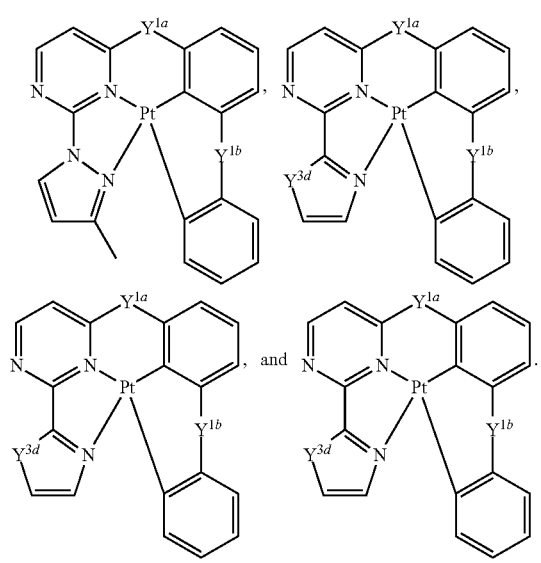

In other aspects, non-limiting examples of specific aspects within this formula can include one or more of the following:

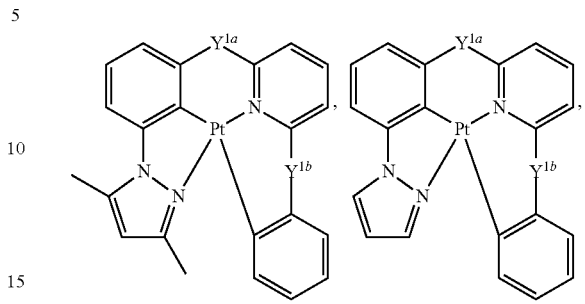

In other aspects, non-limiting examples of specific aspects within this formula can include one or more of the following:

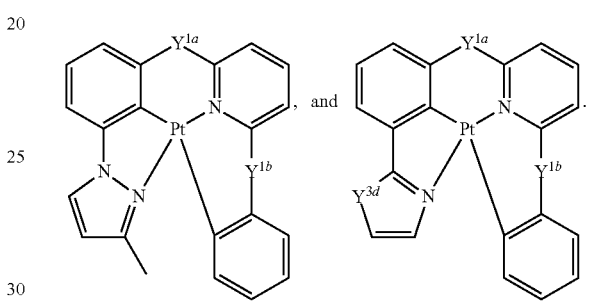

In other aspects, non-limiting examples of specific aspects within this formula can include one or more of the following:

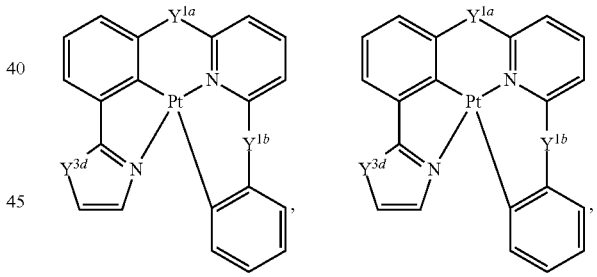

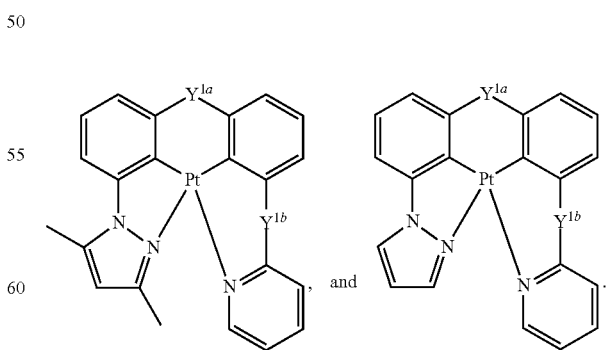

In other aspects, non-limiting examples of specific aspects within this formula can include one or more of the following:

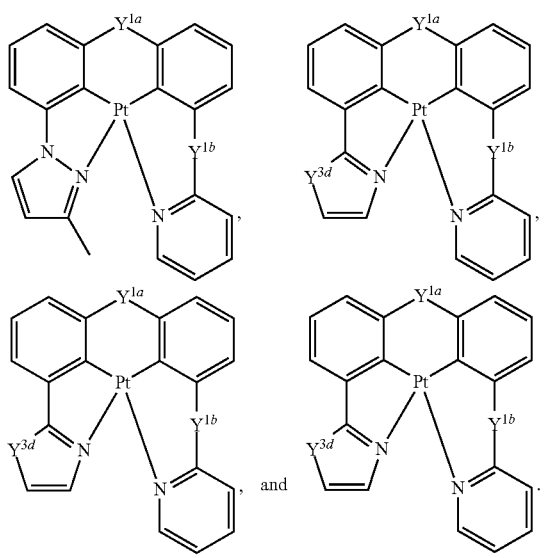

In other aspects, non-limiting examples of specific aspects within this formula can include one or more of the following:

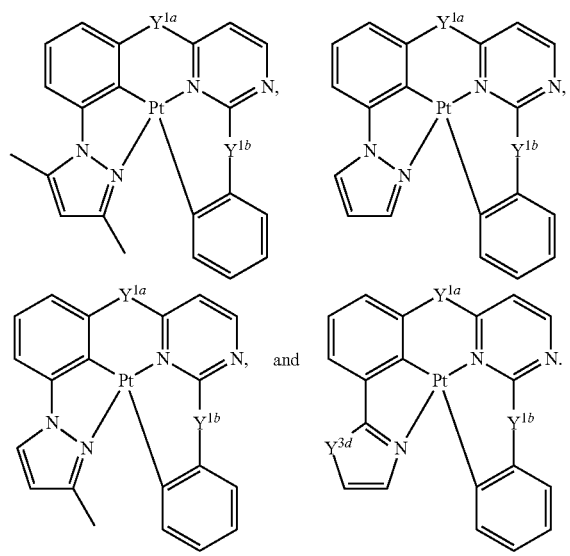

In other aspects, non-limiting examples of specific aspects within this formula can include one or more of the following:

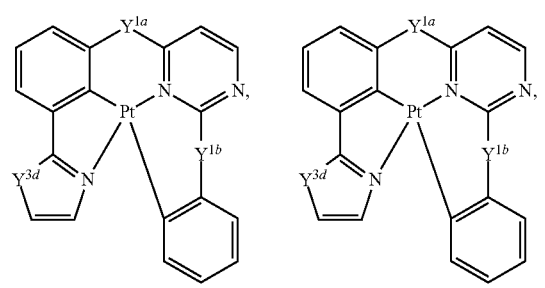

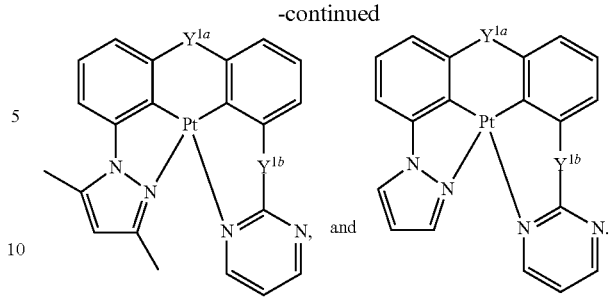

In other aspects, non-limiting examples of specific aspects within this formula can include one or more of the following:

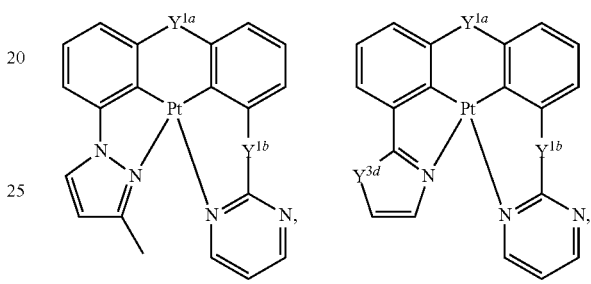

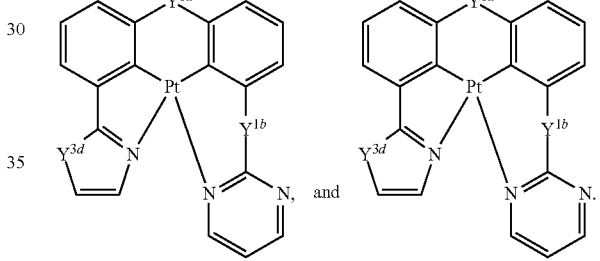

In other aspects, non-limiting examples of specific aspects within this formula can include one or more of the following:

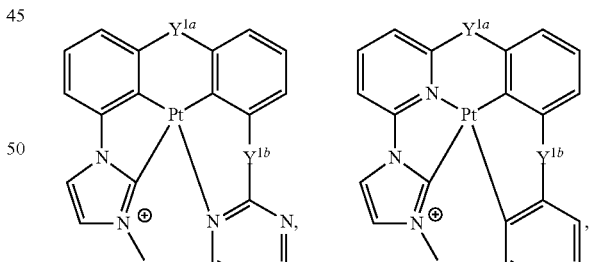

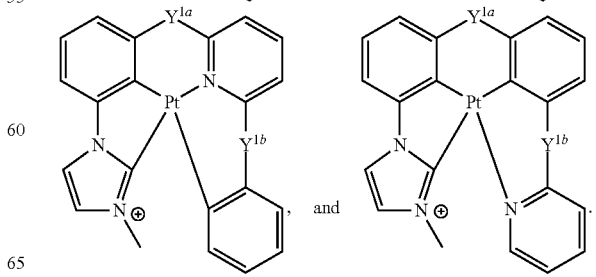

In other aspects, non-limiting examples of specific aspects within this formula can include one or more of the following:

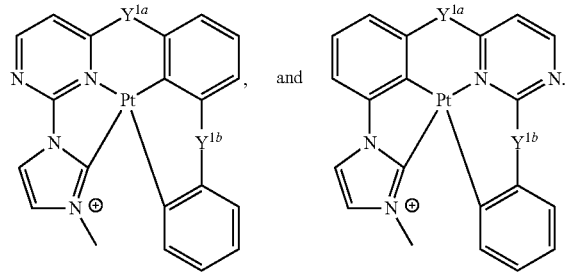

In another aspect of the general formula above, the compound is represented by the formula:

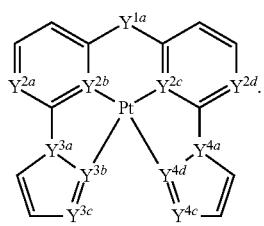

Non-limiting examples of specific aspects within this formula include:

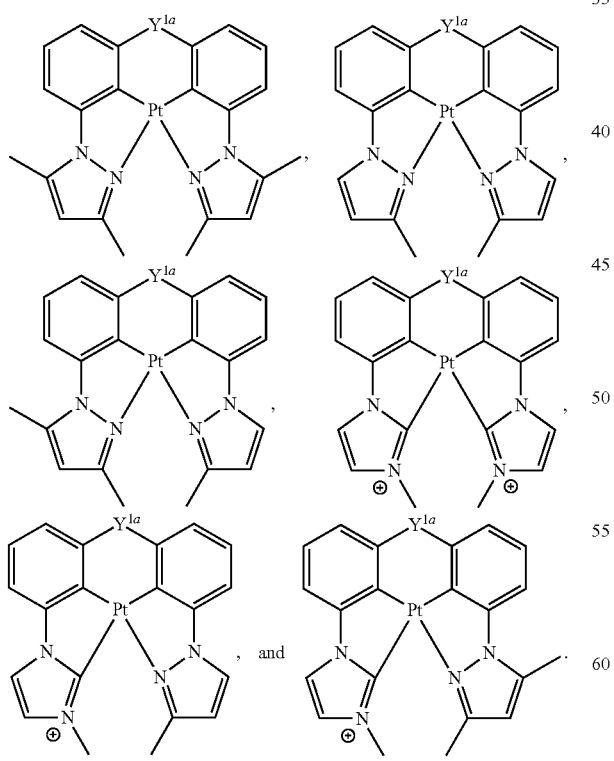

In another aspect of the general formula above, the compound is represented by the formula:

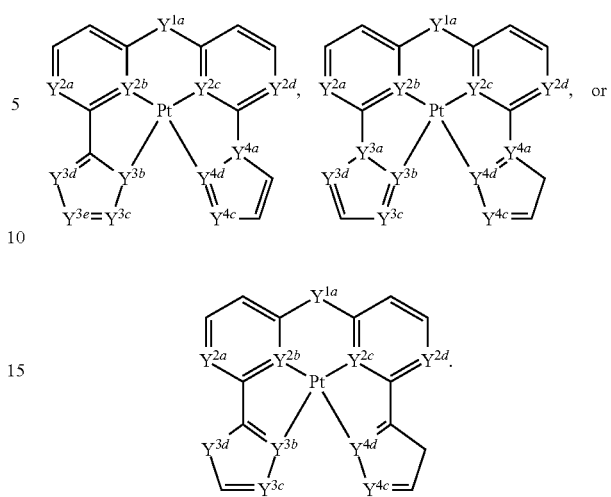

In other aspects, non-limiting examples of specific aspects within these formula can include one or more of the following:

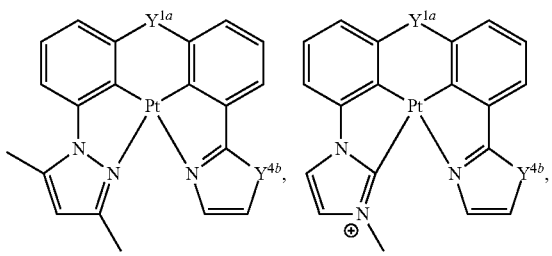

and

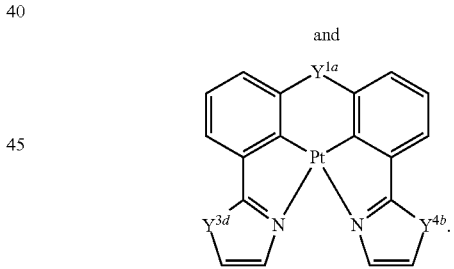

In one aspect, the inventive compound can comprise:

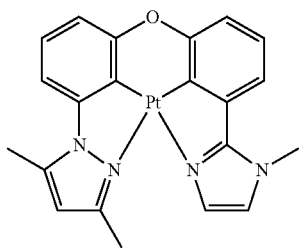

[DMPz-Ph-O-Ph-MIz] Pt(II)

In another aspect, the inventive compound can comprise:

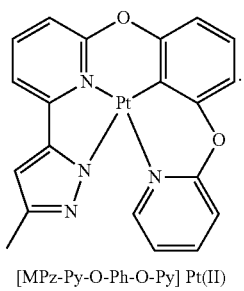

[MPz-Py-O-Ph-O-Py] Pt(II)

In another aspect, the inventive compound can comprise:

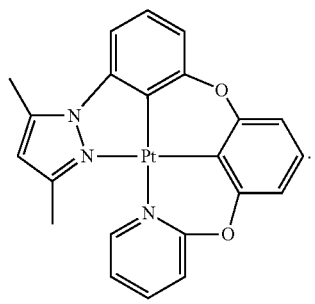

In another aspect, the inventive compound can comprise:

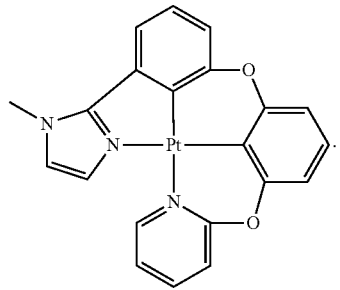

In another aspect, the inventive compound can comprise:

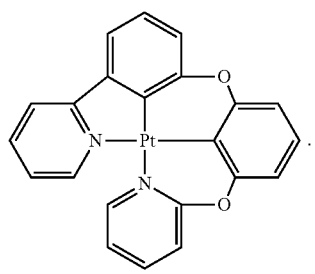

In another aspect, the inventive compound can comprise:

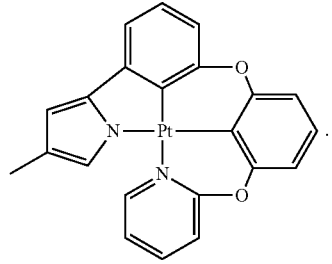

The compounds of the invention can be made using a variety of methods. In one aspect, wherein $Y^{1a}$ is O, the compounds can be provided according to Scheme 1.

Scheme 1.

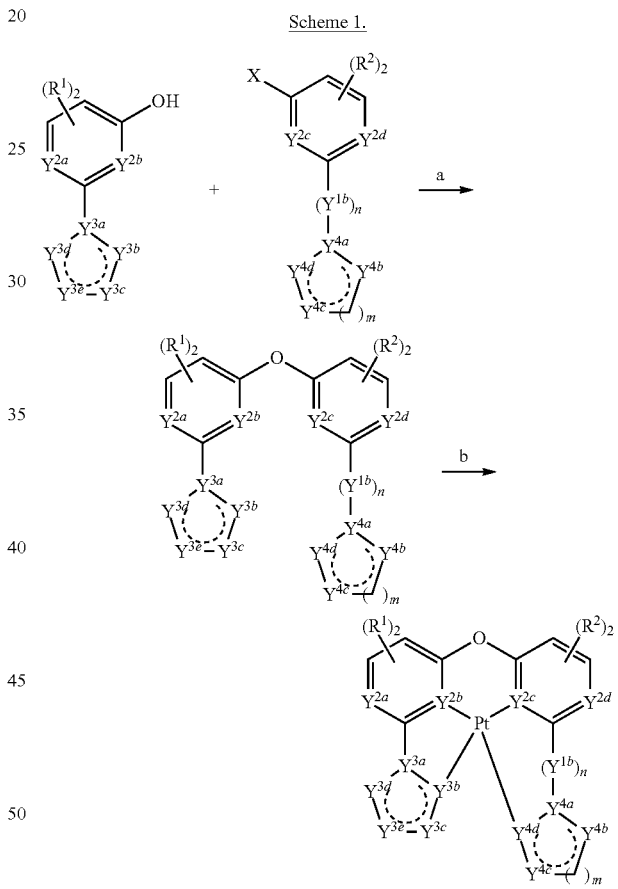

With reference to Scheme 1, step "a" can be accomplished, for example, by using a catalytic amount of a coupling reagent, such as $Cu_2O$, which couples alcohols, particularly phenols, with halogenated phenyl groups. In one aspect, the variable "X" in Scheme 1 above represents halogen (i.e., Cl, F, I, Br), and can be I when used in conjunction with Scheme 1.

Each side of the ligand which complexes the metal can be made independently using a variety of methods, which generally depend on whether $Y^{3a}$ is N or C. In another aspect with reference to Scheme 2 below, when $Y^{4a}$ is N, the precursor can be provided according to Scheme 2(A), wherein a halogenated phenyl compound is reacted with a pyrazole, imadazole, 1H-1,2,3-triazole, 1H-tetrazole, or 2H-pentazole. In one aspect, the halogenated phenyl compound can comprise any halogen (X), including Cl, Br, F, or I, but is preferably I, which is typically more reactive in a coupling reaction. The halogenated phenyl compound and corresponding pyrazole, imadazole, 1H-1,2,3-triazole, 1H-tetrazole, or 2H-pentazole can be coupled using a metallic or organometallic coupling agent, such as $Cu_2O$. During such a coupling reaction, it can be advantageous to include an acid scavenger, such as syn-2-pyridinealdoxime, in a small molar ratio, for example 20 mol %.

Alternatively, when $Y^{4a}$ is C, a different protocol can be used to provide the precursor. In another aspect with reference to Scheme 2(B) below, a halogenated phenyl, as discussed above is reacted with a tetrazole, 1,2,3-triazole, pyrazole, or pyrrole to achieve a carbon-carbon bond coupling, as opposed to a carbon-nitrogen bond coupling as shown in Scheme 2(A). The carbon-carbon bond coupling can also be achieved using an organometallic catalyst, such as a Pd(II) catalyst (e.g., $Pd(OAc)_2$) in a small molar ratio, which is typically used together with an excess of a salt mixture, such as KI and CuI. As one of skill in the art understands, when employing each of the coupling reactions shown in Scheme 2, it can be advantageous to perform the reactions in a dry atmosphere, for example under argon, or even in a dry box to avoid moisture or oxygen inclusion.

Scheme 2.

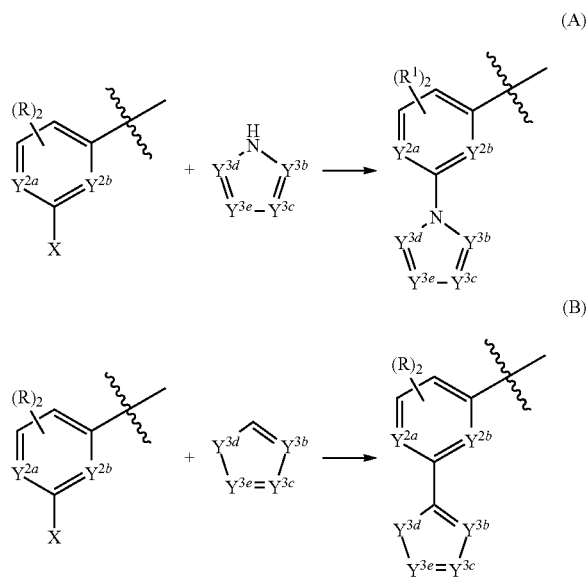

In one aspect, the compounds, reagents, such as, for example, coupling agents, and/or catalysts described herein with respect to the preparation of one or more of the inventive compounds are commercially available. One of skill in the art, in possession of the teachings of this disclosure, could readily select an appropriate compound, reagent, and/or catalyst to prepare a specific inventive compound.

In another aspect, the compounds of the invention can be useful in a variety of optical applications. In one aspect, any one or more of the inventive compounds can be used as an emitter, an absorber, or a combination thereof in an electronic device, such as, for example, a light emitting device. It should be noted that an inventive compound can be used as-is or can be formed into a composite and/or layer to be used in such a device. In one aspect, a layer is formed from one or more inventive compounds, the layer to be positioned in the device. In another aspect, a composite material can be formed using one or more of the inventive compounds, the composite material to be positioned in the device. It should be noted that multiple compounds of the same or varying composition can be utilized within the same layer or composite. In other aspects, a layer or composite can also optionally comprise one or more additional components, such as, for example, a host material, a polymer, a processing aid, a charge transport material, or a combination thereof. In another aspect, multiple layers can be assembled, for example, in overlying registration or substantially overlying registration, to provide desired emissive and/or absorptive properties. For example, multiple layers of differing compounds can be provide to provide a desired emission spectrum. In one aspect, any one or more individual layers in a device, or any portion thereof, can be individually addressable.

In another aspect, the compounds can be useful in organic light emitting diodes (OLED)s, luminescent devices and displays, and other light emitting devices as light emitting materials. With reference to FIG. 1, for example, a specific aspect, [DMPz-Ph-O-Ph-MIz] Pt(II) exhibits photoluminescence (absorption of light followed by emission of light) across a range of wavelengths, including a narrow blue emission and other emission bands in the red to near-IR regions of the spectrum.

The emission (and absorption) profile of the compounds can be tuned by varying the structure of the ligand surrounding the metal center. For example, and while not wishing to be bound by theory, compounds having a ligand with electron withdrawing substituents will generally exhibit different optical properties, including emission and absorption, than compounds having a ligand with electron donating substituents. In one aspect, a chemical structural change can affect the electronic structure of the compound, thereby affecting the absorption and emission of the compound. Thus, in various aspects, the compounds of the present invention can be tailored or tuned to a specific application that desires a particular emission or absorption characteristic.

Figure 2:
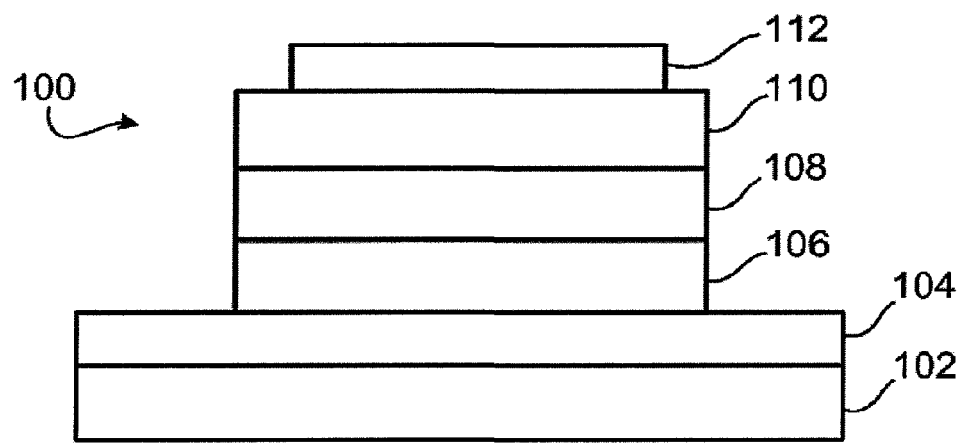
FIG. 2 is a drawing of a cross-section of an exemplary organic light-emitting diode (OLED).
Figure 3:
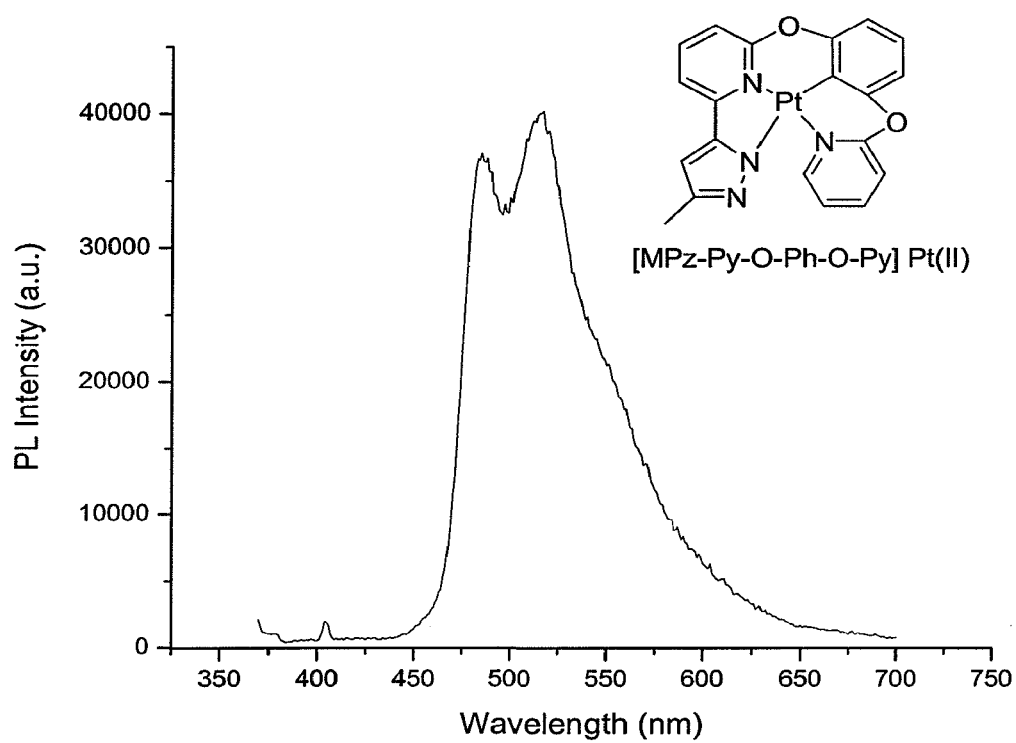
FIG. 3 is a photoluminescence spectrum produced from a specific aspect, [MPz-Py-O-Ph-O-Py] Pt (II) taken in dichloromethane at room temperature.

In one aspect, one or more of the inventive compounds can be used in an OLED. FIG. 2 shows a cross-sectional view of an OLED 100, which includes substrate 102 with an anode 104, which is typically a transparent material, such as indium tin oxide (ITO), a layer of hole-transporting material(s) (HTL) 106, a layer of light processing material 108, such as an emissive material (EML) including an emitter and a host, a layer of electron-transporting material(s) (ETL) 110, and a metal cathode layer 112.

In this aspect, the layer of light processing material 108 can comprise one or more compounds of the present invention optionally together with a host material. The host material can be any suitable host material known in the art. The emission color of an OLED is determined by the emission energy (optical energy gap) of the light processing material 108, which as discussed above can be tuned by tuning the electronic structure of the emitting compounds and/or the host material. Both the hole-transporting material in the HTL layer 106 and the electron-transporting material(s) in the ETL layer 110 can comprise any suitable hole-transporter known in the art. Components and designs for the fabrication of light emitting and/or absorbing devices are commercially available and one of skill in the art could readily select, in possession of the teachings of this disclosure, suitable components and designs to fabricate a device.

It will be apparent that the compounds of the present invention can exhibit phosphorescence. Phosphorescent OLEDs (i.e., OLEDs with phosphorescent emitters) typically have higher device efficiencies that other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

In one aspect, light emitted from an OLED device is typically produced via a fluorescence and/or a phosphorescence process. In various aspects, OLEDs can be comprised of at least two thin organic layers separating the anode and cathode of the device. In one aspect, the material of at least one of these layers can be selected based on the material's ability to transport holes, and the material of at least one other layer can be selected based on its ability to transport electrons.

In another aspect, it can be desirable for OLEDs to be fabricated using materials that provide electroluminescent emission in a relatively narrow band centered near selected spectral regions, corresponding to one or more of the three primary colors so that they may be used as a colored layer in an OLED. In another aspect, it can be desirable that such compounds be capable of being readily deposited as a thin layer using vacuum deposition techniques so that they may be readily incorporated into an OLED that is prepared entirely from vacuum-deposited organic materials. In one aspect, any one or more of the inventive compounds described herein can be formed into a thin layer. In another aspect, any one or more of the inventive compounds described herein can be formed into a thin layer by, for example, a vacuum deposition technique, a thermal deposition technique, a spin-coating technique, or a combination thereof. In other aspects, other coating and/or film forming technologies known in the art can be utilized, provided that such techniques do not destroy and/or adversely affect the light emitting and/or light absorbing properties of the inventive compound.

In one aspect, a general schematic of an exemplary OLED device was described above. In another aspect, the arrangement of layers in an OLED device can comprise a hole transport layer and an electron transporting layer, with an emissive layer therebetween, wherein each of the layers is in at least partially overlying registration. In another aspect, other layers can optionally be present adjacent to or between any other recited layers. In one exemplary aspect, an exciton blocking layer positioned between the emissive layer and the electron transporting layer.

In one aspect, an emissive layer can be formed with a host material in which the emissive molecule are present as a guest or the emissive layer may be formed of the emissive molecule itself. In the former case, the host material may be a hole-transporting matrix, such as, for example, a substituted tri-aryl amine. In another aspect, a host material can comprise 4,4'-N,N'-dicarbazole-biphenyl (CBP).

In yet another aspect, an emissive layer can also contain a polarization molecule that can affects the wavelength of light emitted when a dopant luminesces.

In yet another aspect, a layer formed of an electron transporting material can be used to transport electrons into an emissive layer comprising an emissive molecule and optional host material. In various aspects, an electron transport material can comprise an electron-transporting matrix, such as, for example, metal quinoxolates, oxidazoles and triazoles. In one aspect, an exemplary electron transport material is tris-(8-hydroxyquinoline) aluminum (Alq3).

In another aspect, an exemplary hole transporting material is 4,4'-bis [N-(1-naphthyl)-N-phenyl-amino] biphenyl (NPD).

In one aspect, the use of an exciton blocking layer to confine excitons within a luminescent layer can be advantageous. In one aspect, the blocking layer may be placed between a luminescent layer and an electron transport layer for a hole-transporting host. In one aspect, an exemplary material for such a barrier layer is bathocuproine (BCP).

In one aspect, a layer of one or more inventive compounds can be deposited by thermal evaporation onto substrate, such as, for example, a clean glass substrate, precoated with indium tin oxide. A 400 Å thick layer of 4,4'-bis (N-(1-naphthyl)-N-phenyl-amino] biphenyl can then be used to transport holes to a luminescent layer consisting of Ir (ppy)$_3$ in CBP.

In another aspect, other techniques known to one of ordinary skill can be used in conjunction with the compositions and methods of the present invention. For example, in one aspect, a LiF cathode can be used. In another aspect, a shaped substrate can be used. In yet another aspect, a hole transport material can be used that can result in a reduction in operating voltage or increased quantum efficiency of the resulting device.

The OLED of the present invention may be used in substantially any type of device which is comprised of an OLED, for example, in OLEDs that are incorporated into a larger display, a vehicle, a computer, a television, a printer, a large area wall, theater or stadium screen, a billboard or a sign.

In one aspect, an electronic device, such as, for example, an organic light emitting diode, comprises the following compound as an emitter, an absorber, or a combination thereof:

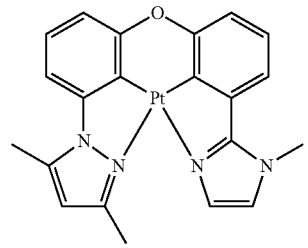

[DMPz-Ph-O-Ph-MIz] Pt(II)

In one aspect, an electronic device, such as, for example, an organic light emitting diode, comprises the following compound as an emitter, an absorber, or a combination thereof:

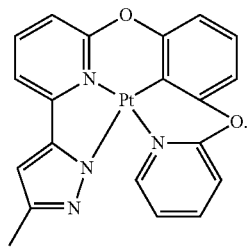

[MPz-Py-O-Ph-O-Py] Pt(II)

In one aspect, an electronic device, such as, for example, an organic light emitting diode, comprises the following compound as an emitter, an absorber, or a combination thereof:

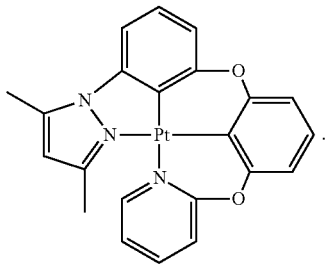

In one aspect, an electronic device, such as, for example, an organic light emitting diode, comprises the following compound as an emitter, an absorber, or a combination thereof:

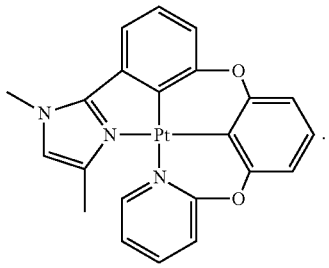

In one aspect, an electronic device, such as, for example, an organic light emitting diode, comprises the following compound as an emitter, an absorber, or a combination thereof:

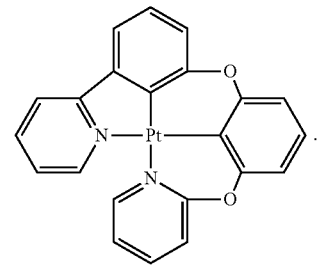

In one aspect, an electronic device, such as, for example, an organic light emitting diode, comprises the following compound as an emitter, an absorber, or a combination thereof:

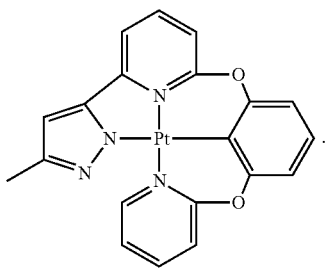

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Preparation of Specific Aspect [(DMPz-Ph)$_2$-O] Pt(II)

Synthesis of DMPz-Ph-OH:

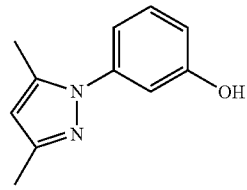

DMPz-Ph-OH

After standard cycles of evacuation and back-fill with dry and pure nitrogen, an oven-dried Schlenk flask equipped with a magnetic stir bar was charged with Cu$_2$O (0.1 mmol, 10 mol %), syn-2-pyridinealdoxime (0.4 mmol, 20 mol %), 3,5-dimethylpyrazole (1.1 mmol), Cs$_2$CO$_3$ (2.5 mmol), 3-iodophenol (1.0 mmol), and anhydrous and degassed dimethylformamide (DMF) (40 mL). The flask was stirred and heated under microwave irradiation for 2 hours. The reaction mixture was allowed to cool to room temperature, diluted with dichloromethane and filtered through a plug of CELITE™, the filter cake being further washed with dichloromethane (20 mL). The filtrate was concentrated under vacuo to yield a residue, which was purified by column chromatography on silica gel to obtain the pure product DMPz-Ph-OH in 50% yield. $^1$H NMR (CDCl$_3$, 500 MHz): δ2.26 (s, 1H), 2.26 (s, 3H), 2.30 (s, 3H), 5.98 (s, 1H), 6.73-6.78 (m, 2H), 7.11 (dd, 1H), 7.18 (dd, 1H).

Synthesis of DMPz-Ph-I:

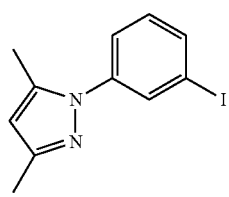

DMPz-Ph-I

After standard cycles of evacuation and back-fill with dry and pure nitrogen, an oven-dried Schlenk flask equipped with a magnetic stir bar was charged with Cu$_2$O (0.1 mmol, 10 mol %), syn-2-pyridinealdoxime (0.4 mmol, 20 mol %), 3,5-dimethylpyrazole (1.1 mmol), Cs$_2$CO$_3$ (2.5 mmol), 1,3-diiodobenzene (1.0 mmol), and anhydrous and degassed acetonitrile (40 mL). The flask was stirred in an oil bath, and refluxed for 2 days. The reaction mixture was allowed to cool to room temperature, diluted with dichloromethane and filtered through a plug of CELITE®, the filter cake being further washed with dichloromethane (20 mL). The filtrate was concentrated under vacuo to yield a residue, which was purified by column chromatography on silica gel to obtain the pure product DMPz-Ph-I in 40% yield. $^1$H NMR (CDCl$_3$, 500 MHz): δ2.30 (s, 3H), 2.32 (s, 3H), 6.00 (s, 1H), 7.22 (dd, 1H), 7.40 (d, 1H), 7.67 (d, 1H), 7.84 (s, 1H).

Synthesis of (DMPz-Ph)$_2$-O:

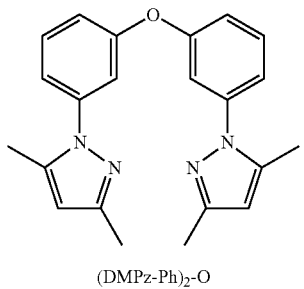

(DMPz-Ph)$_2$-O

After standard cycles of evacuation and back-fill with dry and pure nitrogen, an oven-dried Schlenk flask equipped with a magnetic stir bar was charged with Cu$_2$O (0.1 mmol, 10 mol %), DMPz-Ph-OH (1.0 mmol), K$_2$CO$_3$ (2.5 mmol), DMPz-Ph-I (1.0 mmol), and anhydrous and degassed DMAc (20 mL). The flask was stirred in an oil bath, and refluxed for 2 days. The reaction mixture was allowed to cool to room temperature, diluted with dichloromethane and filtered through a plug of CELITE®, the filter cake being further washed with dichloromethane (20 mL). The filtrate was concentrated under vacuo to yield a residue, which was purified by column chromatography on silica gel to obtain the pure product (DMPz-Ph)$_2$-O in 70% yield. $^1$H NMR (d$_6$-DMSO$_3$, 400 MHz): δ2.66 (s, 6H), 3.29 (s, 6H), 6.29 (s, 2H), 7.14 (dd, 2H), 7.43 (dd, 2H), 7.51 (dd, 2H), 8.16 (dd, 2H).

Synthesis of [(DMPz-Ph)$_2$-O] Pt(11):

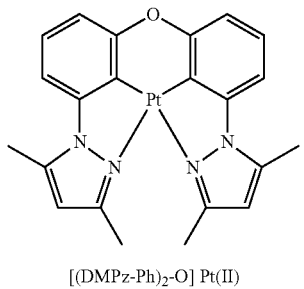

[(DMPz-Ph)$_2$-O] Pt(II)

A mixture of (DMPz-Ph)$_2$-O (1 mmol), K$_2$PtCl$_4$ (0.41 mg, 1 mmol), and acetic acid (10 mL) was refluxed for 3 days. The mixture was allowed to cool to room temperature. The resulting yellow complex was filtered off and washed with MeOH, H$_2$O, EtOH, and Et$_2$O, and dried under vacuum to produce [(DMPz-Ph)$_2$-O] Pt(11) in 90% yield. The product was purified by recrystallization from dimethyl sulfoxide/methanol for further testing.

Example 2

Preparation of Specific Aspect
[DMPz-Ph-O-Ph-MIz] Pt (II)

Synthesis of MIz-Ph-OH:

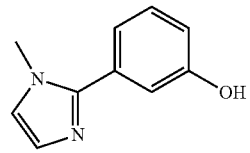

MIz-Ph-OH

A mixture of 3-iodophenol (3.0 mmol), 1-methylimidazole (4.5 mmol), Pd(OAc)$_2$ (5 mg, 0.01 mmol), KI (1.0 g, 6 mmol), and CuI (1.2 g, 6.1 mmol) in degassed DMF (12 mL) was heated under Ar at 140° C. for 5 days. After cooling to room temperature, the mixture was poured into NH$_3$ solution (10%, 50 mL), and CH$_2$Cl$_2$ (40×3 mL) was added. The organic phase was separated and dried (MgSO$_4$), and the solvent was evaporated. The crude product was purified by chromatograph (silica gel; hexanes-Et$_2$O, 4:1) to give MIz-Ph-OH as a light yellow solid (50%).

Synthesis of DMPz-Ph-O-Ph-MIz:

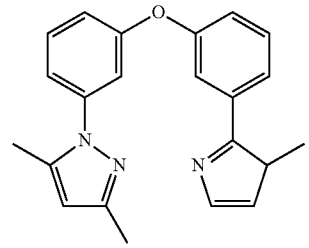

DMPz-Ph-O-Ph-MIz

After standard cycles of evacuation and back-fill with dry and pure nitrogen, an oven-dried Schlenk flask equipped with a magnetic stir bar was charged with Cu$_2$O (0.1 mmol, 10 mol %), DMPz-Ph-OH (1.0 mmol), K$_2$CO$_3$ (2.5 mmol), DMPz-Ph-I (1.0 mmol), and anhydrous and degassed DMAc (20 mL). The flask was stirred in an oil bath, and refluxed for 2 days. The reaction mixture was allowed to cool to room temperature, diluted with dichloromethane and filtered through a plug of CELITE®, the filter cake being further washed with dichloromethane (20 mL). The filtrate was concentrated under vacuo to yield a residue, which was purified by column chromatography on silica gel to obtain the pure product (DMPz-Ph)$_2$-O in 70% yield. $^1$H NMR (CDCl$_3$, 500 MHz): δ2.27 (s, 3H), 2.30 (s, 3H), 3.75 (s, 3H), 5.98 (s, 1H), 6.96 (d, 1H), 7.00 (dd, 1H), 7.07-7.10 (m, 2H), 7.14 (dd, 1H), 7.18 (dd, 1H), 7.32 (d, 1H), 7.37-7.45 (m, 3H).

Synthesis of [DMPz-Ph-O-Ph-MIz] Pt (II):

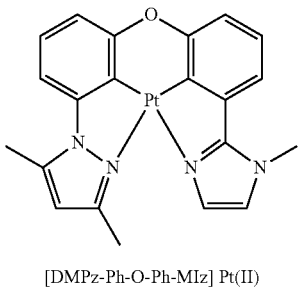

[DMPz-Ph-O-Ph-MIz] Pt(II)

A mixture of DMPz-Ph-O-Ph-MIz (1 mmol), $K_2PtCl_4$ (0.41 mg, 1 mmol), and acetic acid (10 mL) was refluxed for 3 days. The mixture was allowed to cool to room temperature. The resulting yellow complex was filtered off and washed with MeOH, $H_2O$, EtOH, and $Et_2O$, and dried under vacuum to produce [DMPz-Ph-O-Ph-MIz] Pt (II) in 80% yield. The product was purified by recrystallization from dimethyl sulfoxidee/methanol for further testing. $^1$H NMR ($CDCl_3$, 500 MHz): δ 2.65 (s, 3H), 2.72 (s, 3H), 4.08 (s, 3H), 6.41 (s, 1H), 6.88 (d, 1H), 6.99 (s, 1H), 7.12-7.19 (m, 2H), 7.24 (d, 1H), 7.43-7.47 (m, 3H).

Synthesis of [MPz-Py-O-Ph-O-Py] Pt (II):

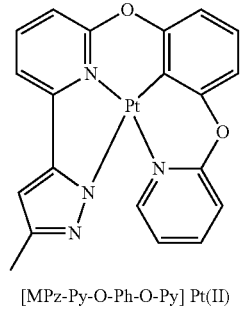

[MPz-Py-O-Ph-O-Py] Pt(II)

A mixture of MPz-Py-O-Ph-O-Py (1 mmol), $K_2PtCl_4$ (1 mmol), and acetic acid (20 mL) was refluxed for 3 days. The mixture was allowed to cool to room temperature. The resulting yellow complex was filtered off and washed with MeOH, $H_2O$, EtOH, and $Et_2O$, and dried under vacuum to produce [MPz-Py-O-Ph-O-Py] Pt (II) in 50% yield. $^1$H NMR ($D_6$-DMSO, 500 MHz): δ2.43 (s,3H), 7.08 (d,1H), 7.13-7.16 (m, 2H), 7.30 (t, 1H), 7.43 (t, 1H), 7.50 (d, 1H), 7.60 (d, 1H), 8.04 (d, 1H), 8.30 (t, 1H), 8.35 (t, 1H), 9.12 (d, 1H).

Example 3

Preparation of Specific Aspect [Py-O-Ph-O-Py-dMPz]Pt (Pt001)

Synthesis of Py-O-Ph-OH

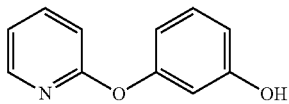 [SMILES: Oc1cccc(Oc2ccccn2)c1]

Under a nitrogen atmosphere, a pressure vessel was charged with a magnetic stir bar, resorcinol (110 mmol), 2-bromopyridine (100 mmol), 1-methylimidazole (5 mmol), and potassium carbonate (200 mmol). Pyridine (80 mL) was added and bubbled with nitrogen for 20 minutes before copper(I) iodide (10 mmol) was added and bubbled 10 minutes further. The vessel was sealed and heated to 140° C. while stirring. After 2 days, the solution was allowed to cool. The solids were filtered off and rinsed with a 50:50 mixture of toluene and methanol. The filtrate was reduced by rotoevaporation and 150 ml of water containing 10 mL glacial acetic acid was added and shaken vigorously. The water was decanted off and 50 mL of dichloromethane was added, forming an off white precipitate which was collected by vacuum filtration and dried with ether, resulting in the pure product Py-O-Ph-OH with a 55% yield. $^1$H NMR ($CDCl_3$): 5.98 (s, 1H), 6.59 (s, 1H), 6.62-6.69 (m, 2H), 6.94 (d, 1H), f7.02 (dd, 1H), 7.23 (vt, 1H), 7.70 (dd, 1H), 8.23 (b, 1H).

Synthesis of Py-O-Ph-O-Ph-Br

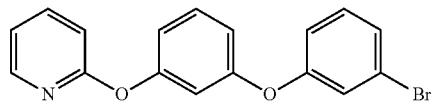 [SMILES: Brc1cccc(Oc2cccc(Oc3ccccn3)c2)c1]

Under a nitrogen atmosphere, a pressure vessel was charged with a magnetic stir bar, Py-O-Ph-OH (50 mmol), 2,6-dibromopyridine (50 mmol), 1-methylimidazole (25 mmol), and potassium carbonate (100 mmol). Toluene (80 mL) was added and bubbled with nitrogen for 20 minutes before copper(I) iodide (5 mmol) was added and the solution bubbled for 10 minutes further. The vessel was sealed and heated to 140° C. while stirring. After 2 days, the solution was allowed to cool and the solids were filtered off and rinsed with dichloromethane. The filtrate was added to a separatory funnel containing dichloromethane and water. The water phase was washed 3 times with 75 mL dichloromethane, and the combined organic layers were washed once with pure water. The organic layer was collected, dried with magnesium sulfate, filtered, and the filtrate reduced by rotoevaporation. The resulting oil was purified by column chromatography using dichloromethane over silica resulting in the pure product Py-O-Ph-O-Ph-Br with a 60% yield. $^1$H NMR ($CDCl_3$): 6.80-6.85 (m, 2H), 6.91 (s, 1H), 6.94 (s, 1H), 6.97-7.03 (m, 2H), 7.19 (vt, 1H), 7.21-7.24 (m, 2H), 7.36 (vt, 1H), 7.70(dd, 1H), 8.21(dd, 1H).

Synthesis of Py-O-Ph-O-Ph-dMPz

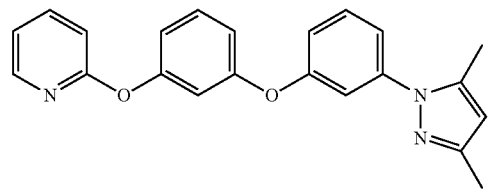 [SMILES: Cc1cc(C)n(-c2cccc(Oc3cccc(Oc4ccccn4)c3)c2)n1]

After standard cycles of evacuation and back-fill with dry and pure nitrogen, an oven-dried Schlenk flask equipped with a magnetic stir bar was charged with $Cu_2O$ (1 mmol, 10 mol %), syn-2-pyridinealdoxime (4 mmol, 20 mol %), 3,5-dimethylpyrazole (12 mmol), $Cs_2CO_3$ (25 mmol), Py-O-Ph-O-Ph-Br (10 mmol), and anhydrous, degassed acetonitrile (100 mL). The solution was refluxed for 2 days, allowed to cool to room temperature, diluted with dichloromethane, and filtered through a plug of Celite. The filter cake was washed with dichloromethane (100 mL) and the filtrate was concentrated under vacuo to yield a residue, which was purified by column chromatography on silica gel to obtain the pure product Py-O-Ph-O-Ph-dMPz in 45% yield. $^1$H NMR (CDCl$_3$): 2.29 (s, 3H), 2.28 (s, 3H), 5.98 (s, 1H), 6.84 (vt, 1H), 6.85-6.93 (m, 3H), 6.98-7.04 (m, 2H), 7.13 (vt, 1H), 7.19 (dd, 1H), 7.35 (vt, 114), 7.39 (vt, 1H), 7.69 (dd, 1H), 8.19 (dd, 1H).

Synthesis of [Py-O-Ph-O-Ph-dMPz]Pt (Pt001)

A mixture of Py-O-Ph-O-Ph-dMPz (1 mmol), K$_2$PtCl$_4$ (0.41 mg, 1 mmol), and acetic acid (35 mL) was refluxed for 3 days. The mixture was allowed to cool to room temperature. The resulting white complex was filtered off and washed with H$_2$O, MeOH, and Et$_2$O, and dried under vacuum to produce [Py-O-Ph-O-Ph-dMPz]Pt in 60% yield. $^1$H NMR (CDCl$_3$): 2.23 (s, 3H), 2.70 (s, 3H), 6.09 (s, 1H), 6.93 (dd, 1H), 7.01 (vt, 1H), 7.03-7.11 (m, 3H), 7.14 (d, 1H), 7.17 (vt, 1H), 7.37 (d, 1H), 7.88 (dd, 1H), 8.80 (d, 1H).

The compound was sublimed under vacuum over a four zone gradient of 220° C.-190° C.-150° C.-110° C. and collected with a 65% yield.

Figure 4:
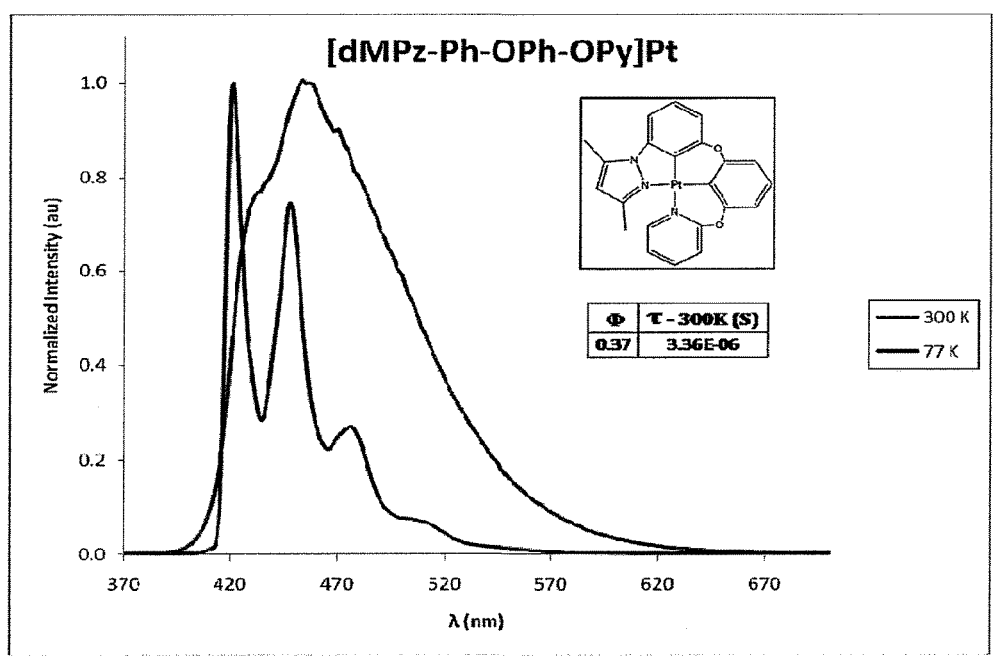
FIG. 4 is a photoluminescence spectrum produced from a specific aspect, [dMPz-Ph-O-Ph-O-Py] Pt taken at 77 K and 300 K.

A photoluminescence spectrum of [Py-O-Ph-O-Py-dMPz]Pt at 77 K and 300 K is illustrated in FIG. 4.

Example 4

Preparation of Specific Aspect [Py-O-Ph-O-Ph-MIz]Pt (Pt002)

Synthesis of Py-O-Ph-O-Ph-MIz

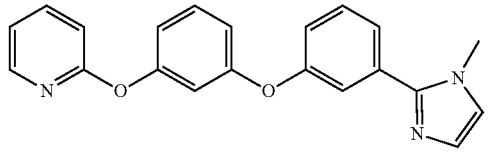 [SMILES: Cn1ccnc1-c1cccc(Oc2cccc(Oc3ccccn3)c2)c1]

Under a nitrogen atmosphere, a 35 mL microwave vial was charged with a magnetic stir bar, Py-O-Ph-O-Ph-Br (10 mmol), copper(I) iodide (20 mmol), and 1-methylimidazole (11 mmol). DMF (15 mL) was added and bubbled with nitrogen for 20 minutes before palladium acetate (.5 mmol) was added and the solution further bubbled for 10 minutes. The vial was sealed and irradiated while stirring at 150 W, 155° C. for 2 hours. The solution was allowed to cool, dumped into a stirring mixture of 100 mL of dichloromethane (DCM) and 150 mL of a 15% aqueous solution of NH$_4$OH for 30 minutes, and poured into a separatory funnel. The organic layer was separated and the aqueous layer was washed twice more with DCM (50 mL). The organic layers were combined and washed once with pure water (50 mL). The organic layer was dried with magnesium sulfate, filtered, and reduced by rotoevaporation. The resulting oil was purified by column chromatography using DCM and methanol over silica resulting in the pure product Py-O-Ph-O-Ph-MIz in an 80% yield. $^1$H NMR (CDCl$_3$): 3.73 (s, 3H) 6.83 (vt, 1H), 6.84-6.93 (m, 3H), 6.96 (d, 1H), 7.00 (dd, 1H), 7.08-7.13 (m, 2H), 7.31 (d, 1H), 7.34 (vt, 1H), 7.41 (d, 1H), 7.42 (vt, 1H), 7.68 (dd, 1H), 8.19 (dd, 1H).

Synthesis of [Py-O-Ph-O-Ph-MIz]Pt (Pt002)

A mixture of Py-O-Ph-O-Ph-MIz (1 mmol), K$_2$PtCl$_4$ (0.41 mg, 1 mmol), and acetic acid (35 mL) was refluxed for 3 days. The mixture was allowed to cool to room temperature. The resulting white complex was filtered off and washed with H$_2$O, MeOH, and Et$_2$O, and dried under vacuum to produce [Py-O-Ph-O-Ph-MIz]Pt in 60% yield. $^1$H NMR (CDCl$_3$): 4.02 (s, 3H), 6.87-6.93 (m, 2H), 7.01 (d, 1H), 7.05-7.13 (m, 4H), 7.17 (vt, 1H), 7.27 (d, 1H), 7.32 (d, 1H), 7.90 (dd, 1H), 8.81 (dd, 1H).

The compound was sublimed under vacuum over a four zone gradient of 220° C.-190° C.-160° C.-130° C. and collected with a 60% yield.

Figure 5:
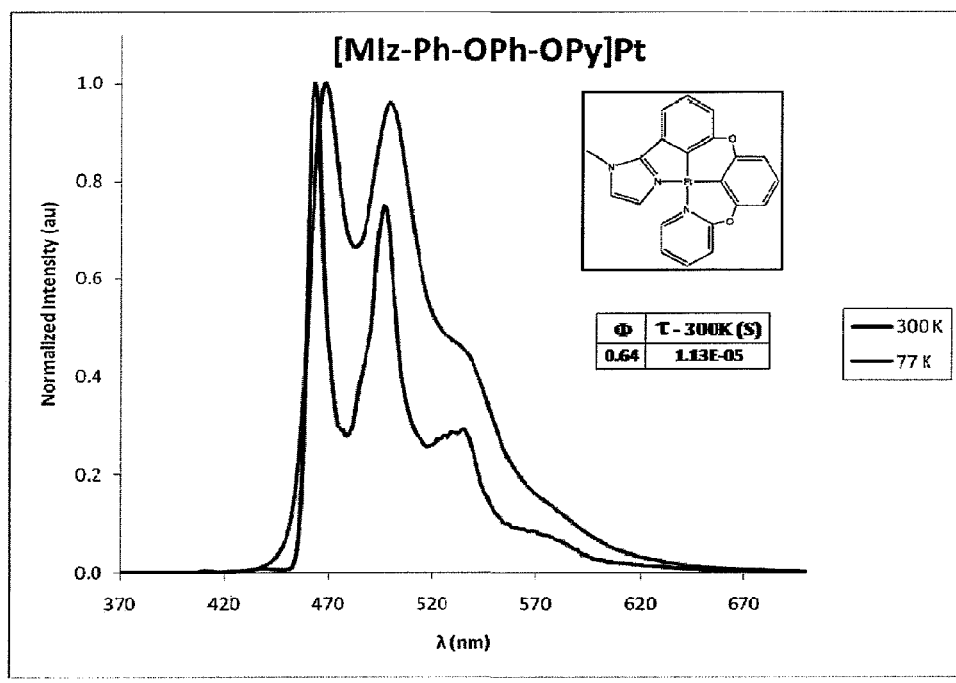
FIG. 5 is a photoluminescence spectrum produced from a specific aspect, [MIz-Ph-O-Ph-O-Py] Pt taken at 77 K and 300 K.

A photoluminescence spectrum of [Py-O-Ph-O-Ph-MIz]Pt at 77 K and 300 K is illustrated in FIG. 5.

Figure 6:
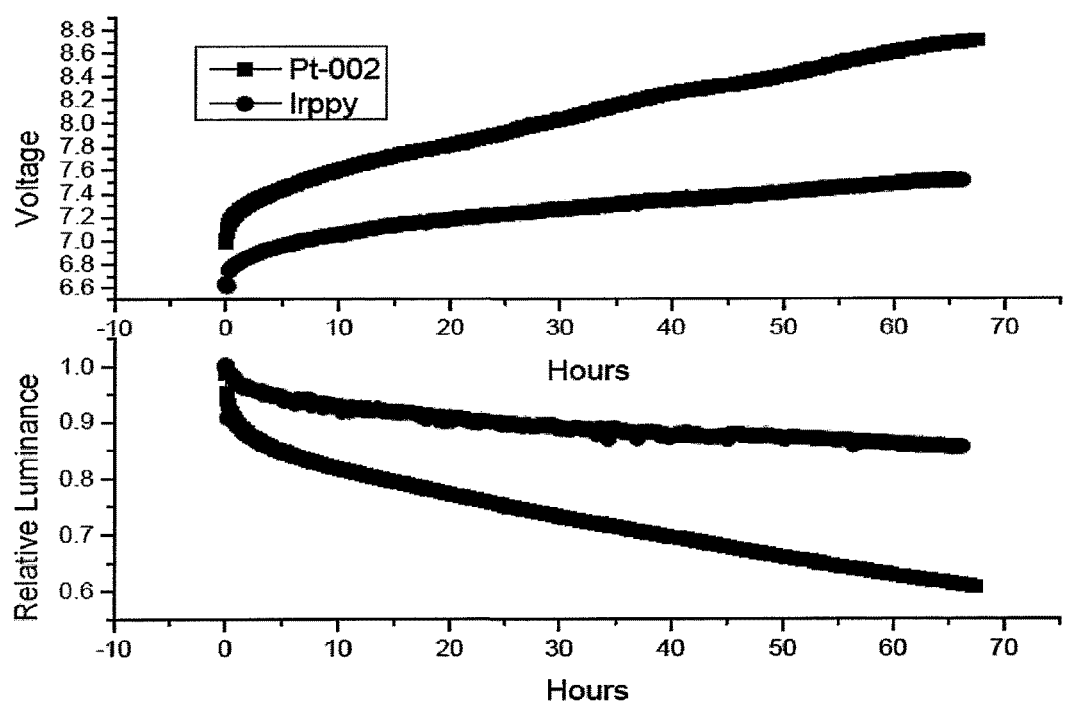
FIG. 6 is a plot of voltage (top) and luminance (bottom) vs. time for an Ir(ppy)$_3$ and Pt002 device.

FIG. 6 illustrates a plot of voltage (top) and luminance (bottom) vs. time for an Ir(ppy)$_3$ and Pt002 device. The general device structure is ITO/CuPc(10 nm)/NPD(30 nm)/25 nm EML(Ir(ppy)$_3$ (6%):CBP or Pt002(2%):CBP)/BAlq (10 nm)/Alq(30 nm)/LiF(1 nm)/Al(100 nm). The device were driven at constant current of 2 mA/cm$^2$.

Example 5

Preparation of Specific Aspect [Py-O-Ph-O-Ph-Py]Pt (Pt003)

Synthesis of Py-O-Ph-O-Ph-Py

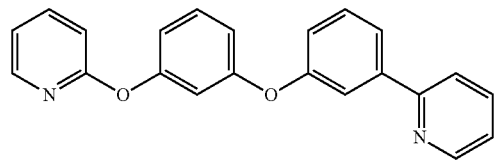 [SMILES: c1ccc(Oc2cccc(Oc3cccc(-c4ccccn4)c3)c2)nc1]

Under a nitrogen atmosphere, an oven dried three neck flask was charged with a magnetic stir bar, Py-O-Ph-O-Ph-Br (10 mmol), and 2-(tripropylstannyl)pyridine (10 mmol). Dry toluene (100 mL) was added and bubbled with nitrogen for 20 minutes before Tetrakis(triphenylphosphine)palladium(0) (.5 mmol) was added, bubbled 10 minutes further, and brought to reflux for 2 days. After cooling, the contents of the flask were filtered, the liquid reduced by rotoevaporation, and the resulting oil was purified by column chromatography using DCM over silica to yield the pure product Py-O-Ph-O-Ph-Py with a 65% yield. $^1$H NMR (CDCl$_3$): 6.84 (vt, 1H), 6.85-6.89 (m, 2H), 6.91(d, 1H), 6.98 (dd, 1H), 7.11 (dd, 1H), 7.24 (dd, 1H), 7.34(vt, 1H), 7.44 (vt, 1H), 7.66-7.78 (m, 5H), 8.19 (dd, 1H), 8.67 (dd, 1H).

Synthesis of [Py-O-Ph-O-Ph-Py]Pt (Pt003)

A mixture of Py-O-Ph-O-Ph-Py (1 mmol), K$_2$PtCl$_4$ (0.41 mg, 1 mmol), and acetic acid (35 mL) was refluxed for 3 days. The mixture was allowed to cool to room temperature. The resulting white complex was filtered off and washed with H$_2$O, MeOH, and Et$_2$O, and dried under vacuum to produce [Py-O-Ph-O-Ph-Py]Pt in 60% yield. $^1$H NMR (CDCl$_3$): 6.95 (dd, 1H), 7.12 (d, 1H), 7.13 (s, 1H), 7.17-7.25 (m, 4H), 7.40 (d, 1H), 7.50 (d, 1H), 7.87-7.97 (m, 3H), 8.47 (d, 1H), 8.63 (d, 1H).

The compound was sublimed under vacuum over a four zone gradient of 185° C.-150° C.-130° C.-100° C. and collected with a 70% yield.

Figure 7:
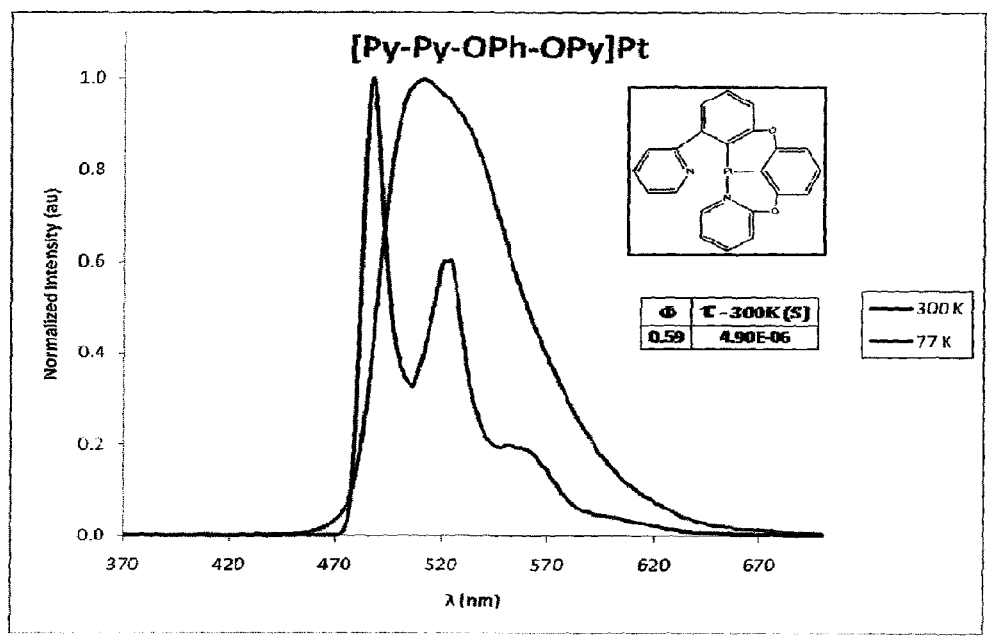
FIG. 7 is a photoluminescence spectrum produced from a specific aspect, [Py-Py-O-Ph-O-Py] Pt taken at 77 K and 300K.

A photoluminescence spectrum of [Py-O-Ph-O-Ph-Py]Pt at 77 K and 300 K is illustrated in FIG. 7.

Example 6

Preparation of Specific Aspect [Py-O-Ph-O-Py-MPz]Pt (Pt004)

Synthesis of Py-O-Ph-O-Py-EA

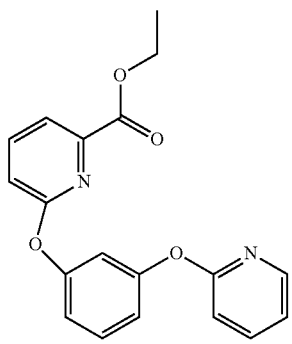 [SMILES: CCOC(=O)c1cccc(Oc2cccc(Oc3ccccn3)c2)n1]

Under a nitrogen atmosphere, a pressure vessel was charged with a magnetic stir bar, Py-O-Ph-OH (20 mmol), Ethyl 6-bromo-2-pyridinecarboxylate (20 mmol), 1-methyl-imidazole (10 mmol), and potassium carbonate (40 mmol). Dry toluene (70 mL) was added and bubbled with nitrogen for 20 minutes before copper(I) iodide (2 mmol) was added and bubbled for 10 minutes further. The vessel was sealed, and heated to 140° C. oil while stirring. After 2 days, the solution was allowed to cool and the solids were filtered off and rinsed with dichloromethane. The filtrate was added to a separatory funnel containing DCM and water. The water phase was washed 3 times with 75 mL DCM, and the combined organic layers were washed once with pure water. The organic layer was collected, dried with magnesium sulfate, filtered, and the filtrate reduced by rotoevaporation. The resulting oil was purified by column chromatography using DCM over silica resulting in the pure product Py-O-Ph-O-Py-EA with a 45% yield. $^1$H NMR (CDCl$_3$): 1.38 (s, 3H), 4.41 (q, 2H), 6.94 (d, 1H), 6.98-7.05 (m, 5H), 7.41 (vt, 1H), 7.69 (dd, 1H), 7.77-7.87 (m, 2H), 8.21 (d, 1H).

Synthesis of Py-O-Ph-O-Py-diKeytone

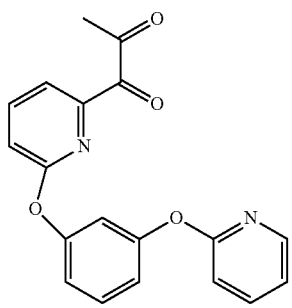 [SMILES: CC(=O)C(=O)c1cccc(Oc2cccc(Oc3ccccn3)c2)n1]

Under a nitrogen atmosphere, an oven dried three neck flask was charged with a magnetic stir bar, sodium methoxide (13 mmol) and dry THF(100 mL). The solution was bubbled with nitrogen for 20 minutes and placed in an ice bath. Dry acetone (11 mmol) was slowly added. After 10 minutes of stirring, Py-O-Ph-O-Py-EA (10 mmol) dissolved in a small amount of dry THF was added. The solution was stirred under nitrogen for 3 hours, brought to room temperature, and refluxed for 3 hours further.

After cooling, 100 mL of DCM with 10 mL of acetic acid was added to the vessel. The solids were filtered off and washed with DCM. The filtrate was collected, reduced by rotoevaporation, and the resulting oil subjected to column chromatography with DCM over silica resulting in the pure product Py-O-Ph-O-PydiKeytone in a 50% yield. $^1$H NMR (CDCl$_3$): 2.15 (s, 3H), 6.60 (s, 1H), 6.94 (d, 1H), 7.00-7.05 (m, 5H), 7.43 (dd, 1H), 7.70 (dd, 1H), 7.81 (s, 1H), 7.82 (d, 1H), 8.21 (d, 1H).

Synthesis of Py-O-Ph-O-Py-MPz

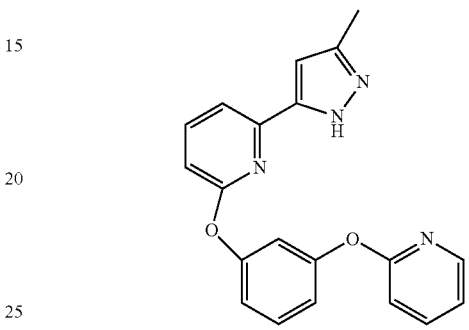

A round bottom flask was charged with a magnetic stir bar, Py-O-Ph-O-Py-diKeytone (10 mmol), and hydrazine (12 mmol) in a 40% solution with water. Ethanol (50 mL) was added and refluxed for 2 hours while stirring under nitrogen and allowed to cool. The cooled solution was dumped into 150 mL of brine which was extracted 3 times with DCM. The combined extractions were dried with magnesium sulfate, filtered, and reduced by rotoevaporation. The resulting oil was subjected to a flash column with DCM over silica giving Py-O-Ph-O-Py-MPz with a 70% yield. $^1$H NMR (CDCl$_3$): 2.30 (s, 31-1), 5.28 (s, .6H), 6.45 (s, 1H), 6.82 (d, 1H), 6.94 (d, 1H), 6.96-7.02 (m, 4H), 7.33 (d, 1H), 7.42 (vt, 1H), 7.67 (q, .4H), 7.68-7.73 (m, 2H), 8.25 (dd, 1H).

Synthesis of [Py-O-Ph-O-Py-MPz]Pt (Pt004)

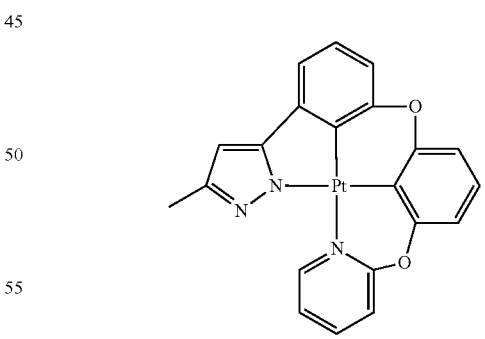

A mixture of Py-O-Ph-O-Py-MPz (1 mmol), K$_2$PtCl$_4$ (0.41 mg, 1 mmol), and acetic acid (35 mL) was refluxed for 3 days. The mixture was allowed to cool to room temperature. The resulting white complex was filtered off and washed with H$_2$O, MeOH, and Et$_2$O, and dried under vacuum to produce [Py-O-Ph-O-Py-MPz]Pt in 80% yield.

Figure 8:
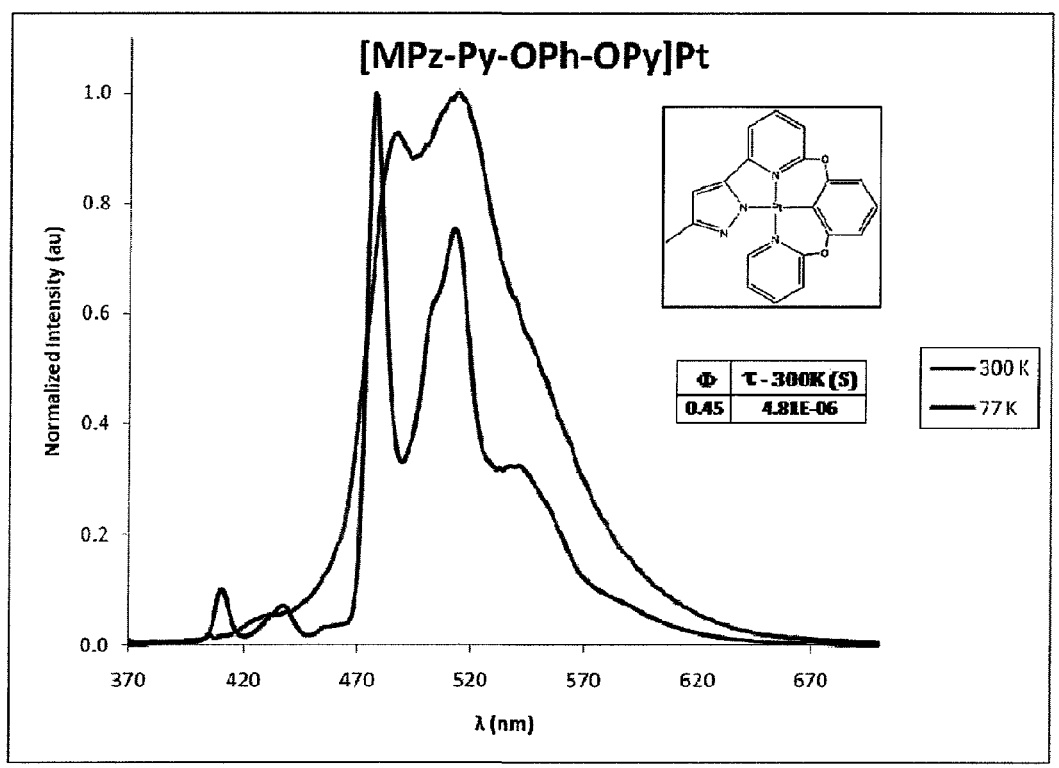
FIG. 8 is a photoluminescence spectrum produced from a specific aspect, [MPz-Py-O-Ph-O-Py] Pt taken at 77 K and 300 K.

A photoluminescence spectrum of [Py-O-Ph-O-Py-MPz]Pt at 77 K and 300 K is illustrated in FIG. 8.

What is claimed is:
1. A compound represented by the formula:

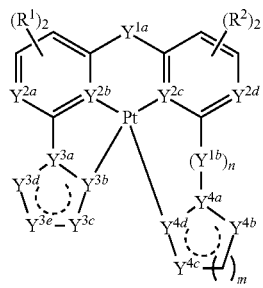

wherein:
each $R^1$ in $(R^1)_2$ independently represents hydrogen, halogen, hydroxyl, amino, nitro, thiol, or optionally substituted $C_1$-$C_4$ alkyl;
each $R^2$ in $(R^2)_2$ independently represents hydrogen, hydroxyl, amino, nitro, thiol, or optionally substituted $C_1$-$C_4$ alkyl;
$Y^{1a}$ represents O, S, $NR^{4a}$, wherein $R^{4a}$ represents optionally substituted $C_1$-$C_4$ alkyl; $Si(R^{4b})_2$, wherein each $R^{4b}$ in $(R^{4b})_2$ independently represents optionally substituted $C_1$-$C_4$ alkyl;
n is 1;
$Y^{1b}$ represents O, S, $NR^{5a}$, wherein $R^{5a}$ represents optionally substituted $C_1$-$C_4$ alkyl; $Si(R^{5b})_2$, wherein each $R^{5b}$ in $(R^{5b})_2$ independently represents optionally substituted $C_1$-$C_4$ alkyl; or $C(R^{5c})_2$, wherein each $R^{5c}$ in $(R^{5c})_2$ represents hydrogen or optionally substituted $C_1$-$C_4$ alkyl;
each of $Y^{2a}$, $Y^{2b}$, $Y^{2c}$, and $Y^{2d}$ independently represents N, $NR^{6a}$, C, or $CR^{6b}$, wherein each of $R^{6a}$ and $R^{6b}$ independently represents hydrogen, optionally substituted $C_1$-$C_4$ alkyl;
each of $Y^{3a}$, $Y^{3b}$, $Y^{3c}$, $Y^{3d}$, $Y^{3e}$, $Y^{4a}$, $Y^{4b}$, $Y^{4c}$, and $Y^{4d}$ independently represents N, $NR^{6a}$, C, or $CR^{6b}$, wherein each of $R^{6a}$ and $R^{6b}$ independently represents hydrogen or optionally substituted $C_1$-$C_4$ alkyl; or $Z(R^{6c})_2$, wherein Z is C or Si, and wherein each $R^{6c}$ in $(R^{6c})_2$ independently represents hydrogen or optionally substituted $C_1$-$C_4$ alkyl;
m is 1 or 2;
the open dotted circle

◌ indicates partial or full unsaturation of the ring with which it is associated; and
the optional substituents for each $C_1$-$C_4$ are selected from the group consisting of alkyl, cycloalkyl, alkoxy, amino, ether, halide, hydroxyl, nitro, silyl, sulfo-oxo, and thiol,
provided that if m is 1, each of $Y^{2a}$ and $Y^{2d}$ is CH and each of $Y^{2b}$ and $Y^{2c}$ is N, then at least one of $Y^{4a}$, $Y^{4b}$, $Y^{3a}$, or $Y^{3d}$ is not N.

2. The compound of claim 1, which is represented by the formula:

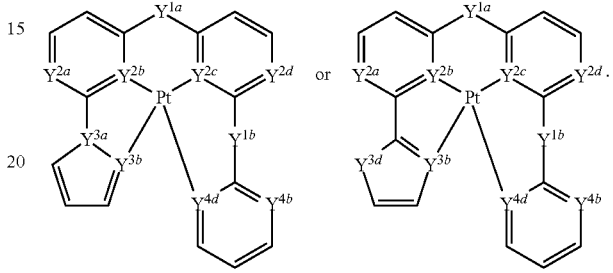

3. An organic light-emitting diode (OLED) comprising the compound of claim 1.
4. An organic light-emitting diode (OLED) comprising, as an emissive material, a compound represented by the formula of claim 1.
5. An organic photovoltaic device comprising the compound of claim 1.
6. An organic photovoltaic device comprising, as a donor or acceptor material, a compound represented by the formula of claim 1.
7. A method for manufacturing an electronic device, the method comprising providing a layer comprising the compound of claim 1, and then positioning the layer in the device.
8. The method of claim 7, wherein the layer is an emissive layer.
9. The method of claim 7, wherein the layer is an absorbing layer.
10. The method of claim 7, wherein the electronic device comprises a light emitting device.
11. The method of claim 7, wherein the electronic device comprises an organic light emitting diode.
12. The method of claim 7, wherein the electronic device comprises a photovoltaic device.

* * * * *

UNITED STATES PATENT AND TRADEMARK OFFICE
CERTIFICATE OF CORRECTION

| | | |
|---|---|---|
| PATENT NO. | : 9,550,801 B2 | Page 1 of 1 |
| APPLICATION NO. | : 14/611654 | |
| DATED | : January 24, 2017 | |
| INVENTOR(S) | : Jian Li et al. | |

It is certified that error appears in the above-identified patent and that said Letters Patent is hereby corrected as shown below:

In the Claims

In Column 35, In Line 38, In Claim 1, delete "$Y^{4c}$," and insert -- $Y^{4c}$, --, therefor.

In Column 35, In Line 39, In Claim 1, delete "$Y^{4d}$independently" and insert -- $Y^{4d}$ independently --, therefor.

In Column 36, In Line 7, In Claim 1, delete "$Y^{2a}$and" and insert -- $Y^{2a}$ and --, therefor.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*